United States Patent
Borate et al.

(10) Patent No.: US 9,512,087 B2
(45) Date of Patent: Dec. 6, 2016

(54) HYBRID MOLECULES CONTAINING PHARMACOPHORES OF FLUCONAZOLE AS ANTIFUNGAL AGENTS AND THEIR PREPARATION

(75) Inventors: Hanumant Bapurao Borate, Pune (IN); Sangmeshwer Prabhakar Sawargave, Pune (IN); Subhash Prataprao Chavan, Pune (IN); Mohan Anand Chandavarkar, Mumbai (IN); Ramkrishnan Ramachaandran Iyer, Mumbai (IN); Amit Chandrakant Tawte, Mumbai (IN); Deepali Damodar Rao, Mumbai (IN)

(73) Assignee: Council for Scientific & Industrial Research, New Delhi (IN)

( * ) Notice: Subject to any disclaimer, the term of this patent is extended or adjusted under 35 U.S.C. 154(b) by 378 days.

(21) Appl. No.: 13/994,323

(22) PCT Filed: Apr. 4, 2012

(86) PCT No.: PCT/IN2012/000244
§ 371 (c)(1),
(2), (4) Date: Jun. 14, 2013

(87) PCT Pub. No.: WO2012/172562
PCT Pub. Date: Dec. 20, 2012

(65) Prior Publication Data
US 2013/0303579 A1    Nov. 14, 2013

(30) Foreign Application Priority Data
Jun. 15, 2011 (IN) .......................... 1750/MUM/2011

(51) Int. Cl.
| | |
|---|---|
| C07D 249/08 | (2006.01) |
| C07D 249/10 | (2006.01) |
| C07D 403/12 | (2006.01) |
| C07D 405/12 | (2006.01) |
| C07D 409/12 | (2006.01) |

(52) U.S. Cl.
CPC ........... *C07D 249/08* (2013.01); *C07D 249/10* (2013.01); *C07D 403/12* (2013.01); *C07D 405/12* (2013.01); *C07D 409/12* (2013.01)

(58) Field of Classification Search
None
See application file for complete search history.

(56) References Cited

U.S. PATENT DOCUMENTS

| | | | |
|---|---|---|---|
| 5,023,258 | A | 6/1991 | Gymer et al. |
| 2004/0192922 | A1* | 9/2004 | Babin et al. |

OTHER PUBLICATIONS

"International Search Report issued for PCT/IN2012/000244 dated Dec. 13, 2012".
Liu, P et al., "Synthesis and SAR studies of biaryloxy-substituted triazoles as antifungal agents", Bioorganic & Medicinal Chemistry Letters, Pergamon, Elsevier Science GB, vol. 18, No. 11, Jun. 1, 2008, 3261-3265, Abstract only.

* cited by examiner

*Primary Examiner* — Savitha Rao
*Assistant Examiner* — Gregg Polansky
(74) *Attorney, Agent, or Firm* — Kramer Amado P.C.

(57) ABSTRACT

Disclosed herein are novel antifungal compounds of Formula 1, containing fluconazole pharmacophore moieties coupled with other moieties including aryl enones and chalcones and pharmaceutically acceptable salts thereof, methods for preparing these compounds and pharmaceutical preparations containing these novel compounds for prevention and treatment of fungal infections.

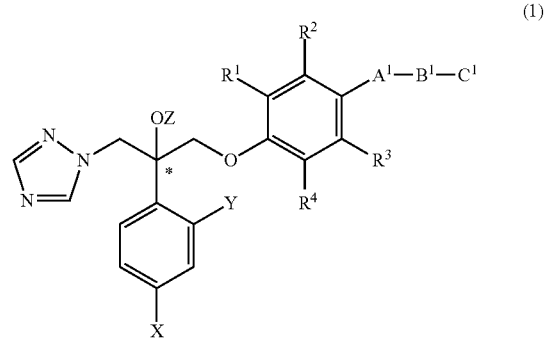

(1)

26 Claims, No Drawings

HYBRID MOLECULES CONTAINING PHARMACOPHORES OF FLUCONAZOLE AS ANTIFUNGAL AGENTS AND THEIR PREPARATION

TECHNICAL FIELD

The present invention discloses novel antifungal compounds of Formula 1, containing fluconazole pharmacophore moieties coupled with other moieties including aryl enones and chalcones and pharmaceutically acceptable salts thereof, methods for preparing these compounds and pharmaceutical preparations containing these novel compounds for prevention and treatment of fungal infections.

Formula 1

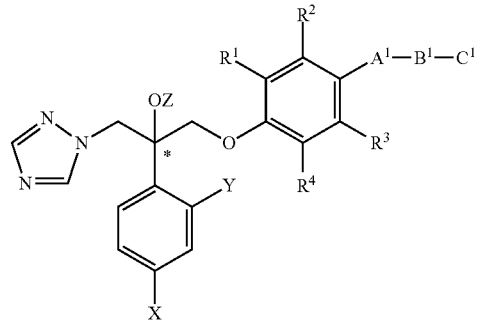

BACKGROUND AND PRIOR ART

The azole group of antifungal agents constitutes an important class of compounds useful in the treatment of various fungal infections. Fluconazole is one of the most important members of the family of azole antifungals as it is orally active and has low toxicity, but its extensive use has resulted in emergence of fluconazole-resistant fungal strains. This has made it necessary to develop analogues of fluconazole effective against resistant strains, and many new compounds have been reported. However, the issues like toxicity, solubility, cost, broad spectrum of activity, etc, make it inevitable to develop superior antifungal agents. The structure-activity relationship studies in case of fluconazole have shown that presence of one triazole ring, halogenated phenyl ring and tertiary alcoholic oxygen functionality is necessary for activity.

Some of the recent references describing synthesis and antifungal activity of fluconazole analogues are described in the following articles:

Chemistry and Biodiversity 4, 1472 (2007); Bioorg. Med. Chem. Lett. 17(13), 3686 (2007); Bioorg. Med. Chem. 16, 7055 (2008); Bioorg. Med. Chem. Lett. 18, 3261 (2008); Bioorg. Med. Chem. Lett. 18, 6538 (2008); Bioorg. Med. Chem. Lett. 19, 2013 (2009); and Bioorg. Med. Chem. Lett. 20, 722 (2010).

The compounds described in the present invention are however new compounds, and there is no prior art available for preparation of these compounds. Thus, the present invention seeks to provide novel azoles containing pharmacophores and their preparation as an effort to come up with antifungal agents with superior antifungal activity.

SUMMARY OF THE INVENTION

Accordingly, to meet the objectives, the present invention discloses novel fluconazole analogues of Formula 1 containing fluconazole pharmacophores, which are useful as antifungal compounds.

In an aspect, the invention provides novel antifungal compounds of Formula 1,

Formula 1

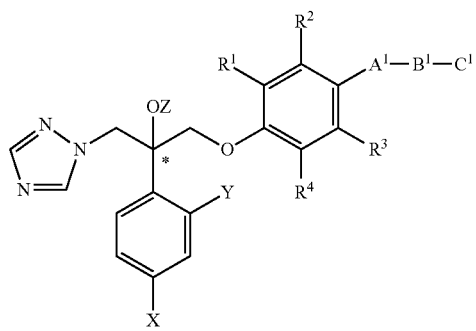

wherein,

X and Y may be same or different, and each represents hydrogen or halogen selected from fluorine, chlorine or bromine.

Z is hydrogen, (un)substituted alkyl, (un)substituted alkenyl, (un)substituted acyl or (un)substituted aryl.

$R^1$, $R^2$, $R^3$ and $R^4$ may be same or different, and each represents hydrogen or functional groups selected from alkyl group of linear or branched chain of 1 to 20 carbon atoms optionally substituted with aryl group, alkoxy (—OR) group (wherein R=alkyl group with 1 to 4 carbon atoms), hydroxyl group, halogen selected from fluorine, chlorine, bromine or iodine, or nitro group.

$A^1$ and $B^1$ are different, and represent —C=O, —CH=CH—, (un)substituted alkyl, cycloalkyl, aziridinyl, epoxy ring, —CH($OR^5$) wherein $R^5$ is H, alkyl, acyl or aryl, —C=N—$OR^6$ wherein $R^6$ is H or alkyl, —C=N—$R^7$ wherein $R^7$ is alkyl or aryl, —C(X'$R^8$)Y'$R^9$ wherein X' and Y' may be same or different and each represents —O or —S, and $R^8$ and $R^9$ represents alkyl or aryl or $R^8$ and $R^9$ are linked with each other to form a (hetero)cyclic five to eight-membered ring; or $A^1$ and $B^1$ together represent heterocyclic ring selected from 3,5-disubstituted (1H)-pyrazole or 3,5-disubstituted 4,5-dihydro(1H)-pyrazole.

$C^1$ represents hydrogen, (un)substituted (hetero) aryl, (un)substituted thienyl, (un)substituted naphthyl, (un)substituted anthracenyl, (un)substituted indolyl, (un)substituted cycloalkyl or (un)substituted alkyl.

"*" is used to designate R or S configuration at carbon atom or racemic nature of the compound.

The present invention further relates to a process for preparation of antifungal compounds of Formula 1, and pharmaceutical preparations containing the antifungal compounds of Formula 1 for prevention and treatment of fungal infections.

DETAILED DESCRIPTION

The invention will now be described in detail in connection with certain preferred and optional embodiments, so that various aspects thereof may be more fully understood and appreciated.

Accordingly, the present invention provides novel antifungal compounds of Formula 1, containing fluconazole pharmacophore moieties and pharmaceutically acceptable salts thereof, methods for preparing these compounds and pharmaceutical preparations containing these novel compounds for prevention and treatment of fungal infections.

The compound of Formula 1 of the present invention is represented as follows;

Formula 1

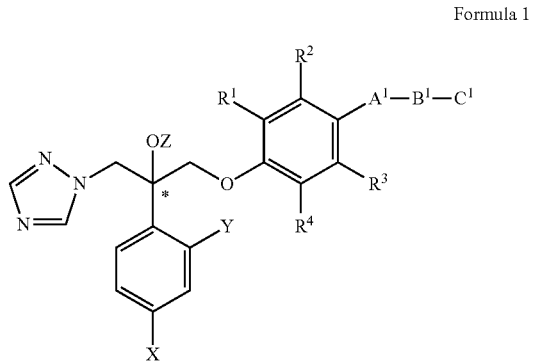

wherein,

X and Y may be same or different, and each represents hydrogen or halogen selected from fluorine, chlorine or bromine.

Z is hydrogen, (un)substituted alkyl, (un)substituted alkenyl, (un)substituted acyl or (un)substituted aryl.

$R^1$, $R^2$, $R^3$ and $R^4$ may be same or different, and each represents hydrogen or functional groups selected from alkyl group of linear or branched chain of 1 to 20 carbon atoms optionally substituted with aryl group, alkoxy (—OR) group (wherein R=alkyl group with 1 to 4 carbon atoms), hydroxyl group, halogen selected from fluorine, chlorine, bromine and iodine, or nitro group.

$A^1$ and $B^1$ are different, and represent —C═O, —CH═CH—, (un)substituted alkyl, cycloalkyl, aziridinyl, epoxy ring, —CH($OR^5$) wherein $R^5$ is H, alkyl, acyl or aryl, —C═N—$OR^6$ wherein $R^6$ is H or alkyl, —C═N—$R^7$ wherein leis alkyl or aryl, —C($X'R^8$)$Y'R^9$ wherein X' and Y' may be same or different and each represents —O or —S, and $R^8$ and $R^9$ represents alkyl or aryl or $R^8$ and $R^9$ are linked with each other to form a (hetero)cyclic five to eight-membered ring; or $A^1$ and $B^1$ together represent heterocyclic ring selected from 3,5-disubstituted (1H)-pyrazole or 3,5-disubstituted 4,5-dihydro(1H)-pyrazole.

$C^1$ represents hydrogen, (un)substituted (hetero)aryl, (un)substituted thienyl, (un)substituted naphthyl, (un)substituted anthracenyl, (un)substituted indolyl, (un)substituted cycloalkyl or (un)substituted alkyl.

'*' is used to designate R or S configuration at carbon atom or racemic nature of the compound.

In an embodiment, the present invention provides antifungal compounds of Formula I, selected from;
- a) compounds of Formula 1A, with a proviso that $A^1$ is —C═O when $B^1$ is —CH═CH—; or $A^1$ is —CH═CH— when $B^1$ is —C═O;
- b) compounds of Formula 1B, with a proviso that $A^1$ is —C═O when $B^1$ is (un)substituted alkyl, epoxy ring; or $A^1$ is (un)substituted alkyl, epoxy ring when $B^1$ is —C═O;
- c) compounds of Formula 1C, with a proviso that $A^1$ is —CH═CH— when $B^1$ is —CH($OR^5$), —C═N—$OR^6$, —C═N—$R^7$, —C($X'R^8$)$Y'R^9$, or $A^1$ is —CH($OR^5$), —C═N—$OR^6$, —C═N—$R^7$, —C($X'R^8$)$Y'R^9$ when $B^1$ is —CH═CH—,
- d) compounds of formula 1D where $A^1$ and $B^1$ together represent 3,5-disubstituted (1H)-pyrazole,
- e) compounds of formula 1E, where $A^1$ and $B^1$ together represent 3,5-disubstituted 4,5-dihydro(1H)-pyrazole, wherein, '*', X, Y, Z, $R^1$, $R^2$, $R^3$, $R^4$, $R^5$, $R^6$, $R^7$, $R^8$, $R^9$, X', Y' and $C^1$ are as defined above.

In another embodiment, the invention provides a process for preparation of the compounds of Formula 1, as described above and which are distinguished in Table 1.

TABLE 1

| Formula | Z | $A^1$ | $B^1$ |
|---|---|---|---|
| 1A | —H, (un)substituted alkyl, (un)substituted alkenyl, (un)substituted acyl or (un)substituted aryl. | —C═O, —CH═CH | —CH═CH—, —C═O |
| 1B | —H, (un)substituted alkyl, (un)substituted alkenyl, (un)substituted acyl or (un)substituted aryl. | —C═O, (un)substituted alkyl, epoxy ring | (un)substituted alkyl, epoxy ring, —C═O |
| 1C | —H, (un)substituted alkyl, (un)substituted alkenyl, (un)substituted acyl or (un)substituted aryl. | —CH($OR^5$), —C═N—$OR^6$, —C═N—$R^7$. —C($X'R^8$)$Y'R^9$ —CH═CH— | —CH═CH—, —CH($OR^5$), —C═N—$OR^6$, —C═N—$R^7$, —C($X'R^8$)$Y'R^9$ |
| 1D | —H, (un)substituted alkyl, (un)substituted alkenyl, (un)substituted acyl or (un)substituted aryl | pyrazole structure | |
| 1E | —H, (un)substituted alkyl, (un)substituted alkenyl, (un)substituted acyl or (un)substituted aryl | dihydropyrazole structure | |

X, Y, $R^1$, $R^2$, $R^3$, $R^4$, $R^5$, $R^6$, $R^7$, $R^8$, $R^9$, X', Y' and $C^1$ are as defined above.

Preparation of Compounds of Formula 1A:

The compounds of Formula 1A of the present invention are prepared by reacting an epoxide of Formula 2 with a compound of Formula 3 in presence of a base, with or without a phase transfer catalyst, to obtain corresponding compound of Formula 4, wherein the base is selected from potassium carbonate, sodium carbonate, cesium carbonate or lithium carbonate, and the phase transfer catalyst is selected from tetra-n-butylammonium bromide (TBAB), tetra-n-butylammonium chloride, benzyltriethylammonium bromide, benzyltriethylammonium chloride, cetyltri-n-butylphosphonium bromide, cetyltrimethylammonium bromide or cetyltrimethylammonium chloride. The compound of Formula 4 is further reacted with a suitable aldehyde/ketone in presence of a base selected from sodium hydroxide, potassium hydroxide, lithium hydroxide, sodium methoxide or potassium tert-butoxide, to obtain the compound of Formula 1A. The preparation of compound of Formula 1A is depicted in Scheme 1 as follows:

Scheme 1:

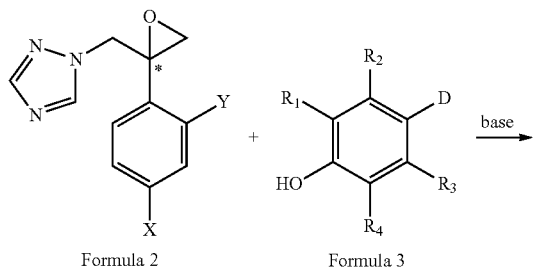

Formula 2     Formula 3

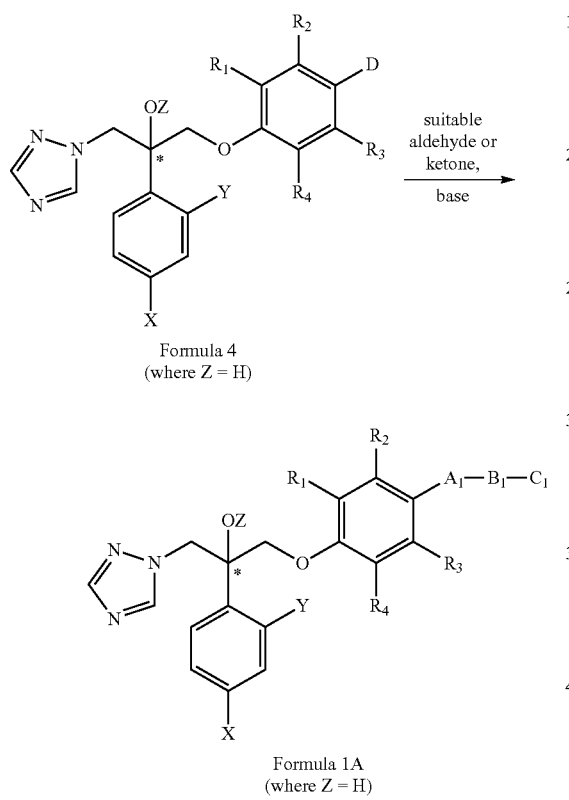

wherein D represents —CHO or —COCH$_3$, and '*', X, Y, R$^1$, R$^2$, R$^3$, R$^4$, R$^5$, R$^6$, R$^7$, R$^8$, R$^9$, X', Y', A$^1$, B$^1$ and C$^1$ are as defined above. The suitable aldehyde/ketone is selected from (un)substituted aliphatic/aromatic/heteroaromatic aldehyde or ketone.

The compounds of Formula 1A can also be obtained by reaction of an epoxide of Formula 2 with a substituted enone of Formula 5 in presence of a base, with or without phase transfer catalyst, wherein the base is selected from potassium carbonate, sodium carbonate, cesium carbonate or lithium carbonate, and the phase transfer catalyst is selected from tetra-n-butylammonium bromide (TBAB), tetra-n-butylammonium chloride, benzyltriethylammonium bromide, benzyltriethylammonium chloride, cetyltri-n-butylphosphonium bromide, cetyltrimethylammonium bromide or cetyltrimethylammonium chloride. The preparation of the compound of Formula 1A is depicted in Scheme 2 as follows:

Scheme 2:

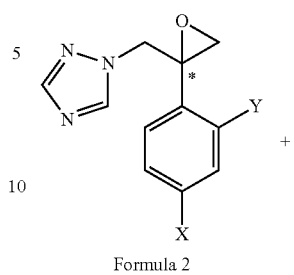

Formula 2

The compounds of Formula 1A where Z is (un)substituted alkyl, (un)substituted alkenyl, (un)substituted acyl or (un)substituted aryl, are prepared by reacting the compounds of formula 1A (where Z is H) with halides of formula 'ZX' (wherein X is halogen selected from iodine, bromine or chlorine) via conversion of tertiary alcoholic group (—OH) to —OZ as depicted in Scheme 3 as follows:

Scheme 3:

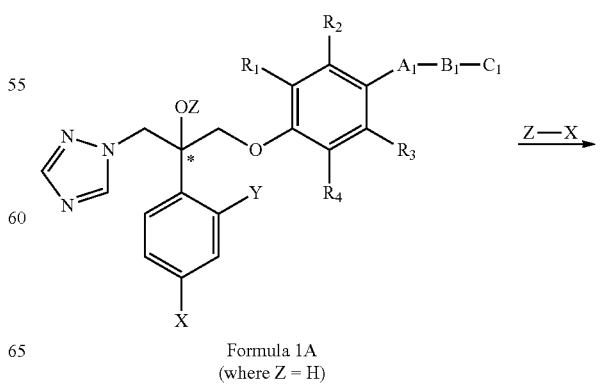

-continued

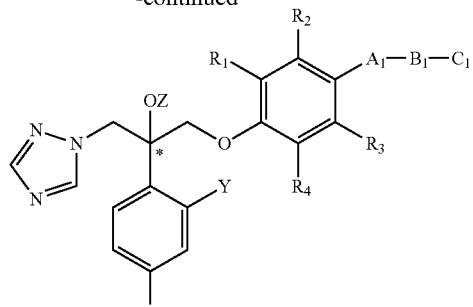

Formula 1A
(where Z = alkyl, alkenyl, acyl or aryl)

Preparation of Compound of Formula 1B:

The compound of Formula 1B of the present invention is prepared by subjecting the compound of Formula 1A to various functional group transformations selected from halogenation, epoxidation or reduction of the unsaturated double bond (—CH═CH—) representing $A^1$ or $B^1$ in the compounds of Formula 1A.

Preparation of Compound of Formula 1C:

The compound of Formula 1C of the present invention is prepared by subjecting the compounds of Formula 1A to various functional group transformations selected from reduction, oximation or ketalization of the carbonyl group representing $A^1$ or $B^1$ in the compounds of Formula 1A.

Preparation of Compound of Formula 1D:

The compound of Formula 1D of the present invention is prepared by reacting compound of Formula 1B with hydrazine hydrate in presence of an acid selected from p-toluene sulfonic acid, acetic acid, propionic acid or trifluoroacetic acid.

Preparation of Compound of Formula 1E:

The compound of Formula 1E of the present invention is prepared by reacting compound of Formula 1A with hydrazine hydrate in presence of an acid selected from p-toluene sulfonic acid, acetic acid, propionic acid or trifluoroacetic acid.

Accordingly, the various compounds of Formula 1 prepared by aforementioned processes are mentioned in Table 2:

TABLE 2

Compounds of Formula 1

| Compound Nos. | $A^1$ | $B^1$ | $C^1$ | $R^1$ | $R^2$ | $R^3$ | $R^4$ | X | Y | Z |
|---|---|---|---|---|---|---|---|---|---|---|
| 1A-1 | —CO— | —CH═CH— | Ph | H | H | H | H | F | F | H |
| 1A-2 | —CO— | —CH═CH— | 4-methoxyphenyl | H | H | H | H | F | F | H |
| 1A-3 | —CO— | —CH═CH— | 2-methoxyphenyl | H | H | H | H | F | F | H |
| 1A-4 | —CO— | —CH═CH— | 3,5-dimethoxyphenyl | H | H | H | H | F | F | H |
| 1A-5 | —CO— | —CH═CH— | 3,4,5-trimethoxyphenyl | H | H | H | H | F | F | H |
| 1A-6 | —CO— | —CH═CH— | 4-chlorophenyl | H | H | H | H | F | F | H |
| 1A-7 | —CO— | —CH═CH— | 2,4-dichlorophenyl | H | H | H | H | F | F | H |
| 1A-8 | —CO— | —H═CH— | 2-fluorophenyl | H | H | H | H | F | F | H |
| 1A-9 | —CO— | —CH═CH— | 4-n-octyloxyphenyl | H | H | H | H | F | F | H |
| 1A-10 | —CO— | —CH═CH— | 4-methoxyphenyl | H | H | H | H | F | H | H |
| 1A-11 | —CO— | —CH═CH— | 4-methoxyphenyl | H | H | H | H | Br | H | H |
| 1A-12 | —CO— | —CH═CH— | 4-chlorophenyl | H | H | H | H | F | H | H |
| 1A-13 | —CO— | —CH═CH— | 2-thienyl | H | H | H | H | F | F | H |
| 1A-14 | —CO— | —CH═CH— | 2-naphthyl | H | H | H | H | F | F | H |
| 1A-15 | —CO— | —CH═CH— | 9-anthracenyl | H | H | H | H | F | F | H |
| 1A-16 | —CO— | —CH═CH— | N-methyl-3-indolyl | H | H | H | H | F | F | H |
| 1A-17 | —CO— | —CH═CH— | 2-thienyl | H | H | H | H | F | H | H |
| 1A-18 | —CO— | —CH═CH— | 2,4-dichlorophenyl | H | H | H | H | F | F | allyl |
| 1A-19 | —CO— | —CH═CH— | 2,4-dichlorophenyl | H | H | H | H | F | F | Me |
| 1B-1 | —CO— | —CHBr—CHBr— | 2,4-dichlorophenyl | H | H | H | H | F | F | H |
| 1C-1 | —CHOH— | —CH═CH— | 2,4-dichlorophenyl | H | H | H | H | F | F | H |
| 1B-2 | —CO— | ![epoxide] | 2,4-dichlorophenyl | H | H | H | H | F | F | H |
| 1D-1 | | ![pyrazole] | 2,4-dichlorophenyl | H | H | H | H | F | F | H |
| 1E-1 | | ![dihydropyrazole] | 2,4-dichlorophenyl | H | H | H | H | F | F | H |
| 1A-20 | —CH═CH— | —CO— | 4-methoxyphenyl | H | H | H | H | F | F | H |
| 1A-21 | —CH═CH— | —CO— | 4-methylphenyl | H | H | H | H | F | F | H |
| 1A-22 | —CH═CH— | —CO— | 2,4-dichlorophenyl | H | H | H | H | F | F | H |
| 1A-23 | —CH═CH— | —CO— | 4-methoxyphenyl | OMe | H | H | H | F | F | H |
| 1A-24 | —CH═CH— | —CO— | 4-n-octyloxyphenyl | H | H | H | H | F | F | H |

TABLE 2-continued

Compounds of Formula 1

| Compound Nos. | A¹ | B¹ | C¹ | R¹ | R² | R³ | R⁴ | X | Y | Z |
|---|---|---|---|---|---|---|---|---|---|---|
| 1A-25 | —CH═CH— | —CO— | methyl | H | H | H | H | F | F | H |
| 1A-26 | —CH═CH— | —CO— | n-pentyl | H | H | H | H | F | F | H |
| 1A-27 | —CH═CH— | —CO— | n-tetradecyl | H | H | H | H | F | F | H |
| 1A-28 | —CH═CH— | —CO— | cyclopropyl | H | H | H | H | F | F | H |
| 1A-29 | —CH═CH— | —CO— | H | OMe | H | H | H | F | F | H |

The present invention provides pharmaceutical compositions comprising a therapeutically effective amount of compound of Formula 1 along with one or more suitable pharmaceutical carriers/excipients.

The present invention relates to the use of the compound of Formula 1 for the treatment or prevention of fungal infections.

The present invention provides a method of treatment or prevention of a fungal infection to a subject by administering an effective amount of the compound of Formula 1 along with one or more suitable pharmaceutical carriers/excipients. The dosage forms include solid dosage forms such as tablets, powders, capsules, liquid dosage forms as well as parenteral dosage forms. The dosage forms can also be prepared as sustained, controlled, modified and immediate release dosage forms. Active ingredient(s) and excipients can be formulated into compositions and dosage forms according to methods known in the art.

The invention is further illustrated with the following examples and should not be construed to limit the scope of the present invention. The features of the present invention will become more apparent from the following description of the inventive concept and the description of the preferred embodiments and appended claims.

EXAMPLES

Example 1

Procedure A: Preparation of (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one (1A-7): (as per Scheme 1)

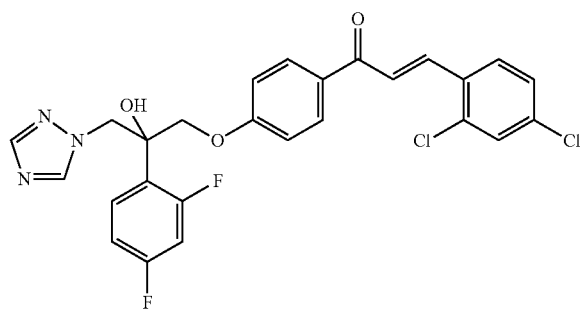 [SMILES: O=C(/C=C/c1ccc(Cl)cc1Cl)c1ccc(OCC(O)(Cn2cncn2)c2ccc(F)cc2F)cc1]

Step 1

To the flame dried K₂CO₃ (1.45 g, 10.54 mmol), were added 1-(4-hydroxyphenyl)ethanone (4.21 mmol), tetra-butyl ammonium bromide (TBAB, 0.5 g) and 1-[2-(2,4-difluorophenyl)-oxiranylmethyl]-1H-[1,2,4]triazole (1.00 g, 4.21 mmol) dissolved in dry ethyl acetate (40 mL). The reaction mixture was allowed to stir under reflux for 12 h under nitrogen atmosphere. It was then cooled to room temperature, diluted with water, extracted with ethyl acetate, concentrated and purified by column chromatography to obtain 1-(4-(2-(2,4-difluorophenyl)-2-hydroxy-3-(1H-1,2,4-triazol-1-yl)propoxy)phenyl)ethanone (Formula 4).

Step 2

To a solution of 1-(4-(2-(2,4-difluorophenyl)-2-hydroxy-3-(1H-1,2,4-triazol-1-yl)propoxy)phenyl)ethanone (1.0 g, 2.68 mmol) of Formula 4 (obtained from Step 1) in methanol (20 ml), 2,4-dichlorobenzaldehyde (0.563 g, 3.21 mmol) was added. To this mixture, aq. sodium hydroxide (10%, 7.5 mL, 0.75 g, 13.5 mmol) was added gradually while stirring. The mixture was stirred at room temperature for 18 h. It was then quenched with ice-cold water, the precipitate obtained was filtered and washed with water followed by aq. HCl (30%). It was then washed again with water, dried and recrystallized from methanol to get pure compound (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one of Formula 1A-7 as pale yellow solid (1.16 g, 82.3%). ¹H NMR (200 MHz, CDCl₃): δ 4.32 (s, 2H), 4.84 (s, 2H), 5.40 (bs, 1H), 6.72-6.90 (m, 4H), 7.18-7.42 (m, 3H), 7.54-7.75 (m, 3H), 7.87-8.02 (m, 3H).

Procedure B: Preparation of (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one (1A-7): (as per scheme 2)

To the flame dried K₂CO₃ (1.45 g, 10.54 mmol), were added (E)-3-(2,4-dichlorophenyl)-1-(4-hydroxyphenyl)prop-2-en-1-one (1.23 g, 4.21 mmol), tetra-butyl ammonium bromide (TBAB, 0.5 g) and 1-[2-(2,4-difluorophenyl)-oxiranylmethyl]-1H-[1,2,4]triazole (1.00 g, 4.21 mmol) dissolved in dry ethyl acetate (40 mL). The reaction mixture was allowed to stir under reflux for 12 h under nitrogen atmosphere. It was then cooled to room temperature, diluted with water, extracted with ethyl acetate, dried over Na₂SO₄, concentrated and purified by column chromatography using pet ether-ethyl acetate (40:60) as eluent to give pure compound (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one of Formula 1A-7 as pale yellow solid (1.82 g, 81.6%). The NMR spectrum was identical with the product obtained by procedure A.

Compounds of Formula 1A and chiral compounds thereof of Formula (R)-1A or (S)-1A can be prepared using procedure A or B.

The compounds prepared according to said procedures are depicted in Table 3 as follows:

TABLE 3

| Compound No. | Compounds | Yield % | ¹H NMR |
|---|---|---|---|
| 1A-1 | 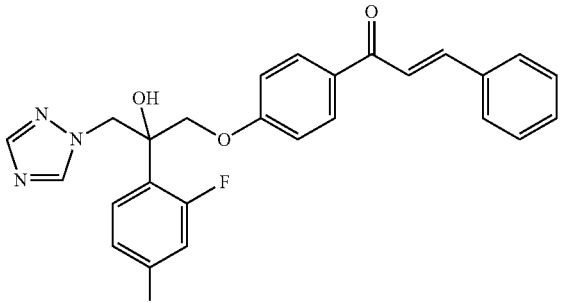<br>(E)-1-(4-(2-(2,4-Difluorophenyl)-2-hydroxy-3-(1H-1,2,4-triazol-1-yl)propoxy)phenyl)-3-phenylprop-2-en-1-one | 80.6 | (200 MHz, CDCl$_3$): δ 4.33 (s, 2H), 4.85 (s, 2H), 5.29 (bs, 1H), 6.73-6.95 (m, 4H), 7.16-7.39 (m, 4H), 7.48 (d, J = 16 Hz, 1H), 7.57-7.79 (m, 4H), 7.96 (d, J = 8 Hz, 2H), 8.06 (s, 1H) |
| 1A-2 | 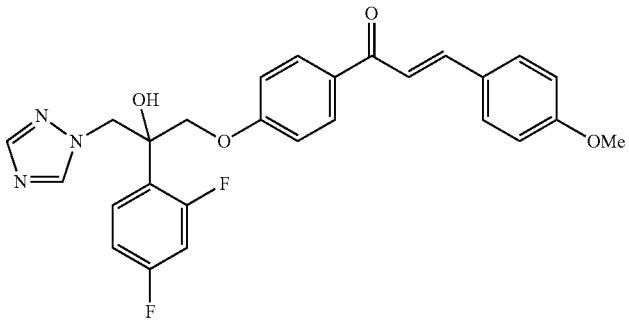<br>E)-1-(4-(2-(2,4-Difluorophenyl)-2-hydroxy-3-(1H-1,2,4-triazol-1-yl)propoxy)phenyl)-3-(4-methoxyphenyl)prop-2-en-1-one | 83.4 | (200 MHz, CDCl$_3$): δ 3.85 (s, 3H), 4.33 (s, 2H), 4.89 (s, 2H), 6.76-7.03 (m, 6H), 7.39 (d, J = 16 Hz, 1H), 7.55-7.73 (m, 3H), 7.81-7.88 (m, 2H), 7.99 (d, J = 10 Hz, 2H), 8.06 (s, 1H) |
| 1A-3 | 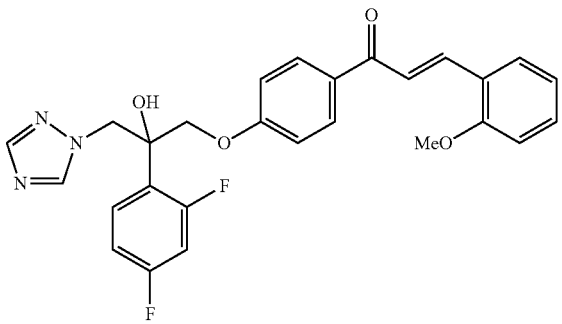<br>(E)-1-(4-(2-(2,4-Difluorophenyl)-2-hydroxy-3-(1H-1,2,4-triazol-1-yl)propoxy)phenyl)-3-(2-methoxyphenyl)prop-2-en-1-one | 81.3 | 200 MHz, CDCl$_3$): δ 3.89 (s, 3H), 4.25-4.33 (m, 2H), 4.73 (bs, 1H), 4.84 (d, J = 14 Hz, 1H), 4.92 (d, J = 14 Hz, 1H), 6.75-7.07 (m, 6H), 7.24 (d, J = 16 Hz, 1H), 7.43-7.69 (m, 6H), 7.84 (s, 1H), 8.04 (s, 1H) |

TABLE 3-continued

| Compound No. | Compounds | Yield % | ¹H NMR |
|---|---|---|---|
| 1A-4 | 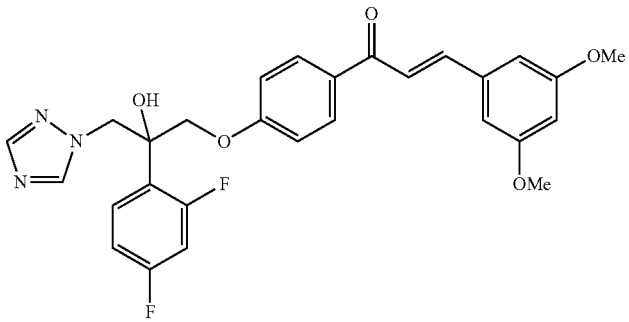<br>(E)-1-(4-(2-(2,4-Difluorophenyl)-2-hydroxy-3-(1H-1,2,4-triazol-1-yl)propoxy)phenyl)-3-(3,5-dimethoxyphenyl)prop-2-en-1-one | 79.7 | (200 MHz, CDCl$_3$): δ 3.82 (s, 6H), 4.32 (bs, 2H), 4.95 (bs, 2H), 5.43 (bs, 1H), 6.51 (s, 1H), 6.75-7.01 (m, 6H), 7.43 (d, J = 16 Hz, 1H), 7.58-7.72 (m, 2H), 7.86-7.98 (m, 3H), 8.59 (s, 1H) |
| 1A-5 | 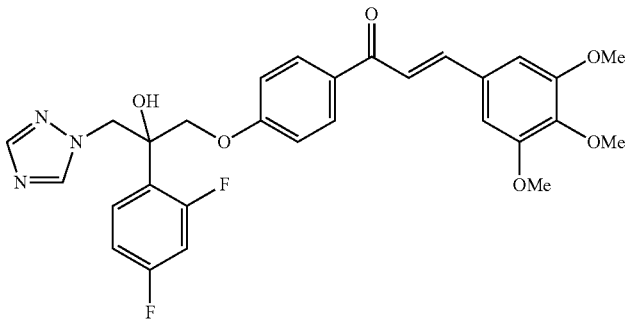<br>(E)-1-(4-(2-(2,4-Difluorophenyl)-2-hydroxy-3-(1H-1,2,4-triazol-1-yl)propoxy)phenyl)-3-(3,4,5-trimethoxyphenyl)prop-2-en-1-one | 78.7 | (200 MHz, CDCl$_3$): δ 3.89 (s, 3H), 3.91 (s, 6H), 4.33 (s, 2H), 4.84 (bs, 1H), 4.88 (s, 2H), 6.75-6.96 (m, 6H), 7.38 (d, J = 16 Hz, 1H), 7.58-7.74 (m, 2H), 7.84 (s, 1H), 7.99 (d, J = 8 Hz, 2H), 8.04 (s, 1H |
| 1A-6 | 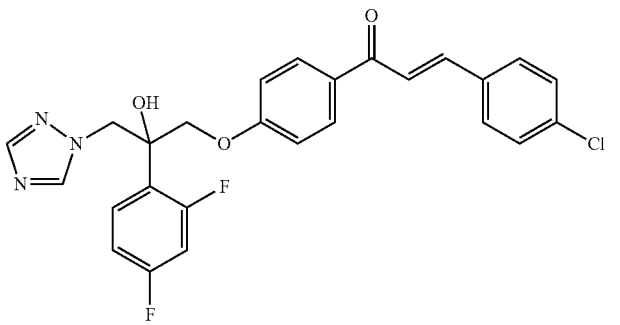<br>(E)-3-(4-Chlorophenyl)-1-(4-(2-(2,4-difluorophenyl)-2-hydroxy-3-(1H-1,2,4-triazol-1-yl)propoxy)phenyl)prop-2-en-1-one | 81.4 | (200 MHz, CDCl$_3$): δ 4.11 (bs, 2H), 4.65 (bs, 2H), 6.53-6.71 (m, 4H), 7.13 (d, J = 8 Hz, 2H), 7.23 (d, J = 16 Hz, 1H), 7.29-7.52 (m, 4H), 7.59 (s, 1H), 7.74 (d, J = 8 Hz, 2H), 7.85 (s, 1H) |

TABLE 3-continued

| Compound No. | Compounds | Yield % | ¹H NMR |
|---|---|---|---|
| 1A-7 | 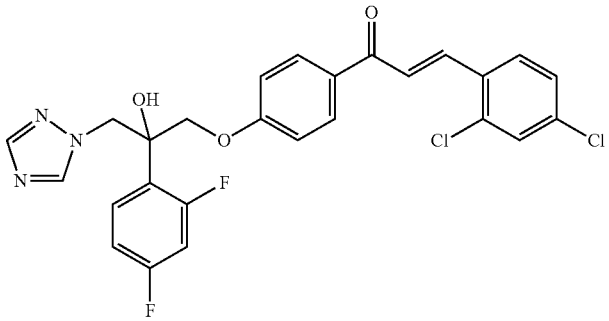<br>(E)-3-(2,4-Dichlorophenyl)-1-(4-(2-(2,4-difluorophenyl)-2-hydroxy-3-(1H-1,2,4-triazol-1-yl)propoxy)phenyl)prop-2-en-1-one | 82.3 | (200 MHz, CDCl$_3$): δ 4.32 (s, 2H), 4.84 (s, 2H), 5.40 (bs, 1H), 6.72-6.90 (m, 4H), 7.18-7.42 (m, 3H), 7.54-7.75 (m, 3H), 7.87-8.02 (m, 3H). |
| 1A-8 | 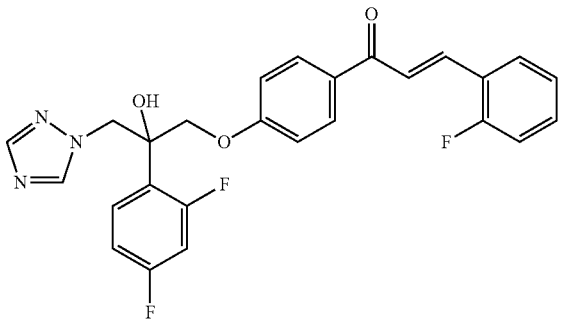<br>(E)-1-(4-(2-(2,4-Difluorophenyl)-2-hydroxy-3-(1H-1,2,4-triazol-1-yl)propoxy)phenyl)-3-(2-fluorophenyl)prop-2-en-1-one | 82.5 | (200 MHz, CDCl$_3$): δ 4.33 (bs, 2H), 4.86 (bs, 2H), 6.73-6.83 (m, 2H), 6.89 (d, J = 8 Hz, 2H), 7.04-7.19 (m, 2H), 7.29-7.40 (m, 1H), 7.54-7.68 (m, 3H), 7.80 (s, 1H), 7.85 (d, J = 16 Hz, 1H), 7.92 (d, J = 8 Hz, 2H), 8.07 (s, 1H) |
| 1A-9 | 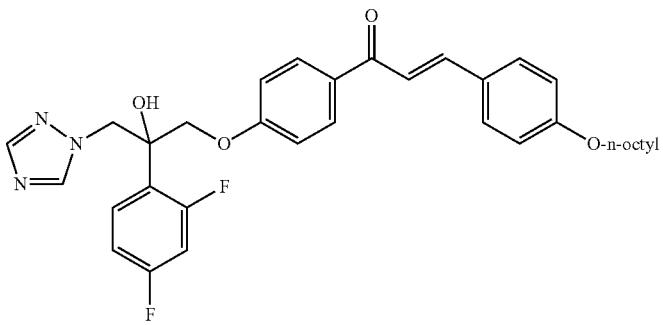<br>(E)-1-(4-(2-(2,4-Difluorophenyl)-2-hydroxy-3-(1H-1,2,4-triazol-1-yl)propoxy)phenyl)-3-(4-(octyloxy)phenyl)prop-2-en-1-one | 81.2 | ¹H NMR (200 MHz, CDCl$_3$): δ 0.90 (t, J = 6 Hz, 3H), 1.26-1.50 (m, 10H), 1.74-1.87 (m, 2H), 4.00 (t, J = 8 Hz, 2H), 4.33 (bs, 2H), 4.71 (bs, 1H), 4.82-4.98 (m, 2H), 6.76-6.98 (m, 6H), 7.40 (d, J = 16 Hz, 1H), 7.57-7.71 (m, 3H), 7.78 (d, J = 16 Hz, 1H), 7.86 (s, 1H), 7.99-8.04 (m, 3H) |

TABLE 3-continued

| Compound No. | Compounds | Yield % | ¹H NMR |
|---|---|---|---|
| 1A-10 | 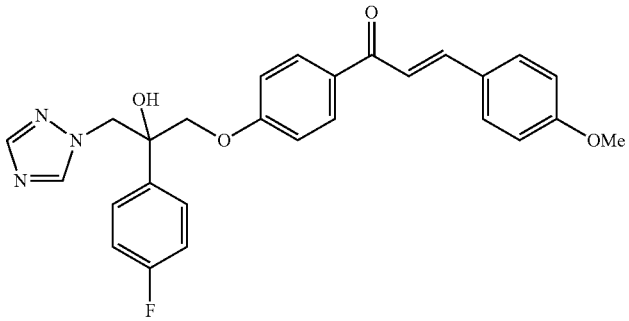<br>(E)-1-(4-(2-(4-Fluorophenyl)-2-hydroxy-3-(1H-1,2,4-triazol-1-yl)propoxy)phenyl)-3-(4-methoxyphenyl)prop-2-en-1-one | 80.1 | (200 MHz, CDCl$_3$): δ 3.86 (s, 3H), 4.14 (d, J = 10 Hz, 1H), 4.21 (d, J = 10 Hz, 1H), 4.47 (bs, 1H), 4.62 (d, J = 14 Hz, 1H), 4.78 (d, J = 14 Hz, 1H), 6.91-6.98 (m, 4H), 7.01-7.13 (m, 2H), 7.40 (d, J = 16 Hz, 1H), 7.49-7.64 (m, 4H), 7.78 (d, J = 16 Hz, 1H), 7.89-8.04 (m, 4H) |
| 1A-11 | 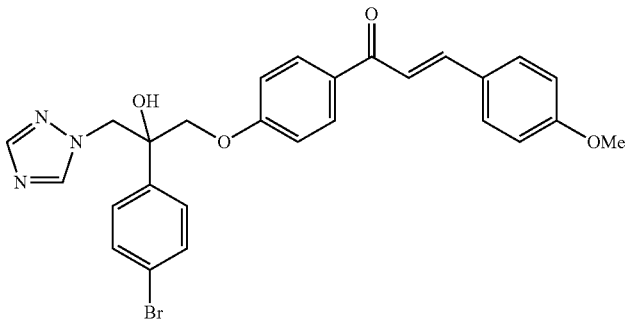<br>(E)-1-(4-(2-(4-Bromophenyl)-2-hydroxy-3-(1H-1,2,4-triazol-1-yl)propoxy)phenyl)-3-(4-methoxyphenyl)prop-2-en-1-one | 79.3 | (200 MHz, CDCl$_3$): δ 3.86 (s, 3H), 4.11-4.21 (m, 2H), 4.60 (d, J = 14 Hz, 1H), 4.64 (bs, 1H), 4.77 (d, J = 14 Hz, 1H), 6.90-6.96 (m, 4H), 7.34-7.53 (m, 5H), 7.59 (d, J = 8 Hz, 2H), 7.77 (d, J = 16 Hz, 1H), 7.91 (s, 1H), 7.99 (s, 1H), 8.00 (d, J = 8 Hz, 2H). |
| 1A-12 | 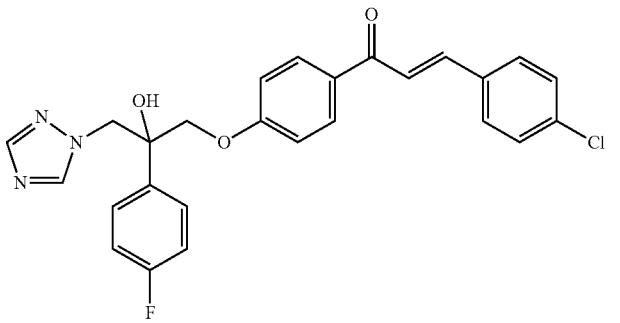<br>(E)-3-(4-Chlorophenyl)-2-(4-(2-(4-fluorophenyl)-2-hydroxy-3-(1H-1,2,4-triazol-1-yl)propoxy)phenyl)prop-2-en-1-one | 79.2 | (200 MHz, CDCl$_3$): δ 4.14 (d, J = 10 Hz, 1H), 4.21 (d, J = 10 Hz, 1H), 4.50 (bs, 1H), 4.62 (d, J = 14 Hz, 1H), 4.78 (d, J = 14 Hz, 1H), 6.93-7.11 (m, 4H), 7.35-7.60 (m, 7H), 7.75 (d, J = 16 Hz, 1H), 7.89-8.03 (m, 4H). |

TABLE 3-continued

| Compound No. | Compounds | Yield % | ¹H NMR |
|---|---|---|---|
| 1A-13 | 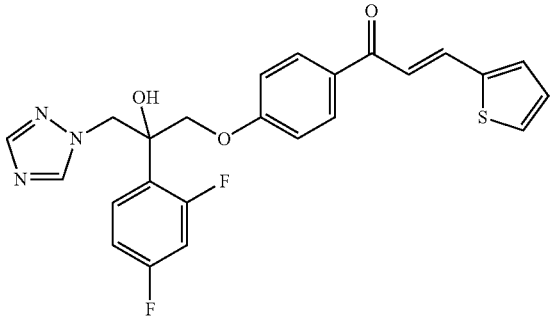<br>(E)-1-(4-(2-(2,4-Difluorophenyl)-2-hydroxy-3-(1H-1,2,4-triazol-1-yl)propoxy)phenyl)-3-(thiophen-2-yl)prop-2-en-1-one | 80.3 | (200 MHz, CDCl$_3$): δ 4.33 (bs, 2H), 4.87 (bs, 2H), 5.04 (bs, 1H), 6.75-6.94 (m, 4H), 7.04-7.11 (m, 1H), 7.25-7.42 (m, 3H), 7.57-7.70 (m, 1H), 7.82 (s, 1H), 7.87-7.98 (m, 3H), 8.06 (s, 1H) |
| 1A-14 | 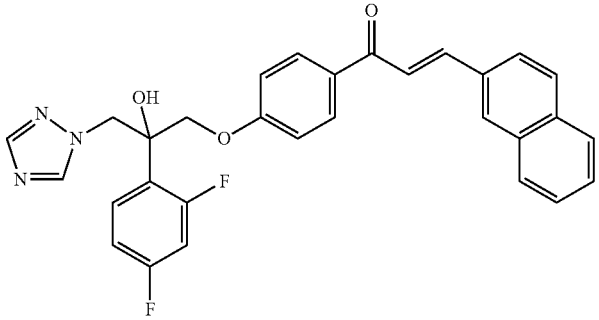<br>(E)-1-(4-(2-(2,4-Difluorophenyl)-2-hydroxy-3-(1H-1,2,4-triazol-1-yl)propoxy)phenyl)-3-(naphthalen-2-yl)prop-2-en-1-one | 83.2 | (200 MHz, CDCl$_3$): δ 4.28 (d, J = 8 Hz, 1H), 4.43 (d, J = 10 Hz, 1H), 5.01 (d, J = 14 Hz, 1H), 5.18 (d, J = 14 Hz, 1H), 6.79-6.88 (m, 2H), 6.96 (d, J = 8 Hz, 2H), 7.44-7.55 (m, 4H), 7.57 (d, J = 16 Hz, 1H), 7.76-8.00 (m, 8H), 8.22 (s, 1H) |
| 1A-15 | 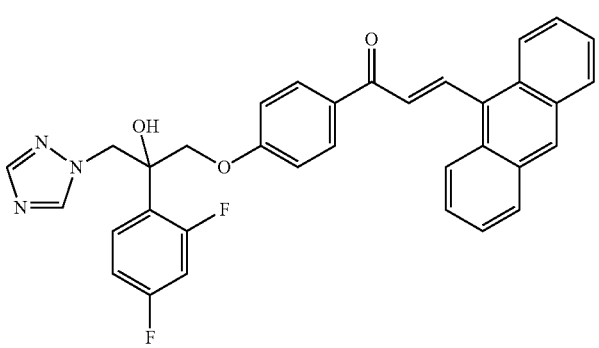<br>(E)-3-(Anthracen-9-yl)-1-(4-(2-(2,4-difluorophenyl)-2-hydroxy-3-(1H-1,2,4-triazol-1-yl)propoxy)phenyl)prop-2-en-1-one | 77.2 | (200 MHz, CDCl$_3$): δ 4.08-4.19 (m, 2H), 4.56 (bs, 1H), 4.72-4.90 (m, 2H), 6.55 (d, J = 8 Hz, 2H), 6.74-6.91 (m, 2H), 7.34-7.63 (m, 8H), 7.83-7.96 (m, 4H), 7.99 (s, 1H), 8.03-8.12 (m, 2H), 8.31 (s, 1H) |

TABLE 3-continued

| Compound No. | Compounds | Yield % | ¹H NMR |
|---|---|---|---|
| 1A-16 | 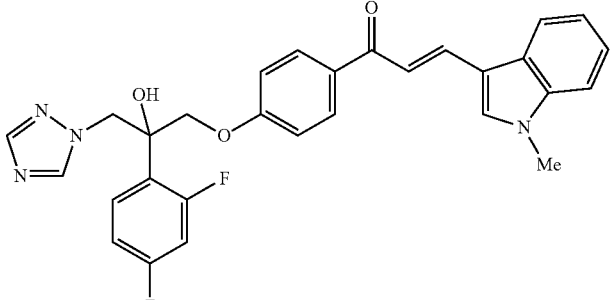<br>(E)-1-(4-(2-(2,4-Difluorophenyl)-2-hydroxy-3-(1H-1,2,4-triazol-1-yl)propoxy)phenyl)-3-(1-methyl-1H-indol-3-yl)prop-2-en-1-one | 80.7 | (200 MHz, CDCl$_3$): δ 3.82 (s, 3H), 4.31-4.39 (m, 2H), 4.81-4.96 (m, 3H), 6.76-6.88 (m, 2H), 6.95 (d, J = 10 Hz, 2H), 7.28-7.39 (m, 4H), 7.44 (s, 1H), 7.52 (d, J = 14 Hz, 1H), 7.59-7.71 (m, 1H), 7.85 (s, 1H), 7.96-8.10 (m, 4H) |
| 1A-17 | 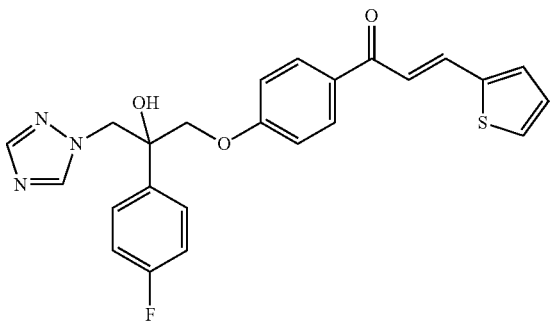<br>(E)-1-(4-(2-(4-Fluorophenyl)-2-hydroxy-3-(1H-1,2,4-triazol-1-yl)propoxy)phenyl)-3-(thiophen-2-yl)prop-2-en-1-one<br>(E)-3-(2,4-dichlorophenyl)-1-(4-(2-(2,4-difluorophenyl)-2-methoxy-3-(1H-1,2,4-triazol-1-yl)propoxy)phenyl)prop-2-en-1-one. | 78.4 | (200 MHz, CDCl$_3$): δ 4.14 (d, J = 10 Hz, 1H), 4.21 (d, J = 10 Hz, 1H), 4.62 (d, J = 14 Hz, 1H), 4.78 (d, J = 14 Hz, 1H), 6.93 (d, J = 10 Hz, 2H), 7.02-7.12 (m, 3H), 7.35-7.43 (m, 3H), 7.47-7.57 (m, 2H), 7.88-8.03 (m, 5H). |
| 1A-20 | 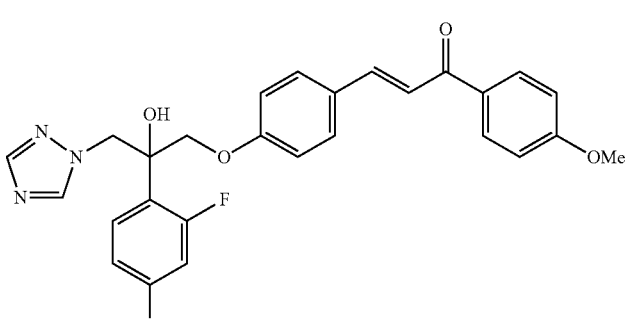<br>(E)-3-(4-(2-(2,4-Difluorophenyl)-2-hydroxy-3-(1H-1,2,4-triazol-1-yl)propoxy)phenyl)-1-(4-methoxyphenyl)prop-2-en-1-one | 82.7 | δ 3.89 (s, 3H), 4.25-4.33 (m, 2H), 4.71 (bs, 1H), 4.81-4.96 (m, 2H), 6.76-7.00 (m, 6H), 7.43 (d, J = 16 Hz, 1H), 7.56-7.66 (m, 3H), 7.75 (d, J = 16 Hz, 1H), 7.86 (s, 1H), 8.00-8.05 (m, 3H) |

TABLE 3-continued

| Compound No. | Compounds | Yield % | $^1$H NMR |
|---|---|---|---|
| 1A-21 | 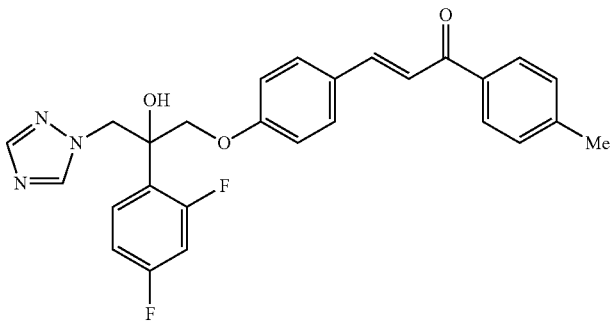<br>(E)-3-(4-(2-(2,4-Difluorophenyl)-2-hydroxy-3-(1H-1,2,4-triazol-1-yl)propoxy)phenyl)-1-(p-tolyl)prop-2-en-1-one | 83.4 | (200 MHz, CDCl$_3$): δ 2.43 (s, 3H), 4.24-4.35 (m, 2H), 4.77 (s, 1H), 4.80-4.95 (m, 2H), 6.75-6.93 (m, 4H), 7.29 (d, J = 8 Hz, 2H), 7.41 (d, J = 16 Hz, 1H), 7.54-7.66 (m, 3H), 7.75 (d, J = 14 Hz, 1H), 7.84 (s, 1H), 7.92 (d, J = 8 Hz, 2H), 8.04 (s, 1H) |
| 1A-22 | 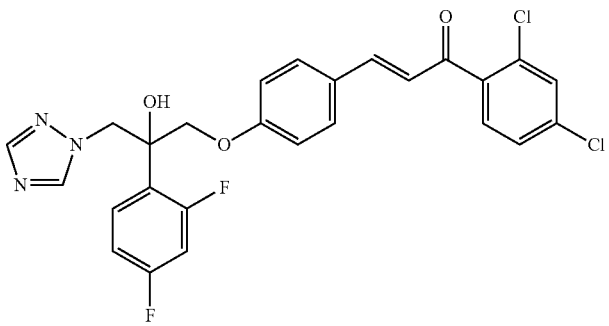<br>E)-1-(2,4-Difluorophenyl)-3-(4-(2-(2,4-difluorophenyl)-2-hydroxy-3-(1H-1,2,4-triazol-1-yl)propoxy)phenyl)prop-2-en-1-one | 81.1 | (200 MHz, CDCl$_3$): δ 4.27 (s, 2H), 4.82 (s, 2H), 5.22 (bs, 1H), 6.71-6.84 (m, 4H), 6.92 (d, J = 16 Hz, 1H), 7.25-7.46 (m, 6H), 7.53-7.62 (m, 1H), 7.75 (s, 1H), 8.04 (s, 1H). |
| 1A-23 | 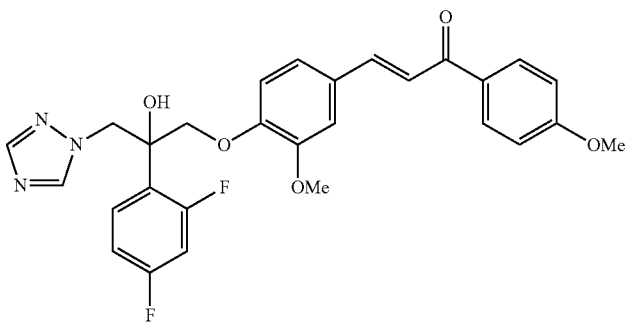<br>(E)-3-(4-(2-(2,4-Difluorophenyl)-2-hydroxy-3-(1H-1,2,4-triazol-1-yl)propoxy)-3-methoxyphenyl)-1-(4-methoxyphenyl)prop-2-en-1-one | 78.1 | (500 MHz, CDCl$_3$): δ 3.85 (s, 6H), 4.30 (d, J = 8 Hz, 1H), 4.33 (d, J = 8 Hz, 1H), 4.83 (d, J = 12 Hz, 1H), 4.88 (d, J = 12 Hz, 1H), 5.11 (bs, 1H), 6.75-6.83 (m, 2H), 6.87 (d, J = 8 Hz, 1H), 6.95 (d, J = 8 Hz, 2H), 7.10-7.16 (m, 2H), 7.39 (d, J = 15 Hz, 1H), 7.56-7.61 (m, 1H), 7.69 (d, J = 15 Hz, 1H), 7.77 (s, 1H), 8.00 (d, J = 8 Hz, 2H), 8.08 (s, 1H). |

| Compound No. | Compounds | Yield % | ¹H NMR |
|---|---|---|---|
| 1A-24 | 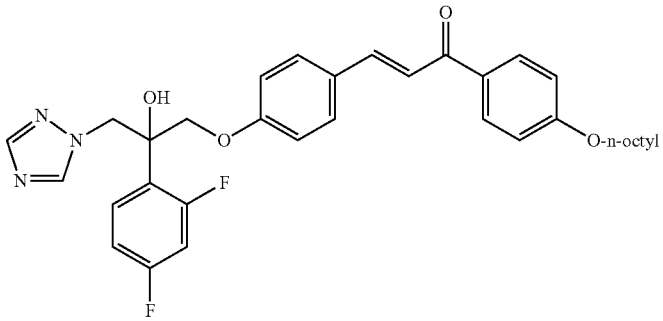<br>(E)-3-(4-(2-(2,4-Difluorophenyl)-2-hydroxy-3-(1H-1,2,4-triazol-1-yl)propoxy)phenyl)-1-(4-(octyloxy)phenyl)prop-2-en-1-one | 80.7 | (200 MHz, CDCl₃): δ 0.89 (t, J = 6 Hz, 3H), 1.28-1.51 (m, 10H), 1.75-1.88 (m, 2H), 4.04 (t, J = 8 Hz, 2H), 4.25-4.35 (m, 2H), 4.72 (bs, 1H), 4.80-4.96 (m, 2H), 6.75-6.98 (m, 6H), 7.43 (d, J = 16 Hz, 1H), 7.55-7.65 (m, 3H), 7.75 (d, J = 16 Hz, 1H), 7.85 (s, 1H), 7.99-8.04 (m, 3H). |
| 1A-25 | 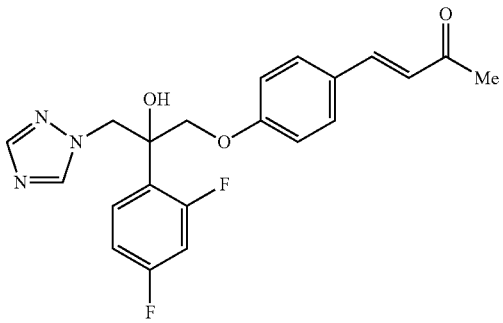<br>(E)-4-(4-(2-(2,4-Difluorophenyl)-2-hydroxy-3-(1H-1,2,4-triazol-1-yl)propoxy)phenyl)but-3-en-2-one | 47.3 | (200 MHz, CDCl₃): δ 2.35 (s, 3H), 4.28 (s, 2H), 4.79-4.94 (m, 2H), 6.59 (d, J = 16 Hz, 1H), 6.74-6.89 (m, 5H), 7.40-7.48 (m, 2H), 7.56-7.69 (m, 1H), 7.82 (s, 1H), 8.04 (s, 1H). |
| 1A-26 | 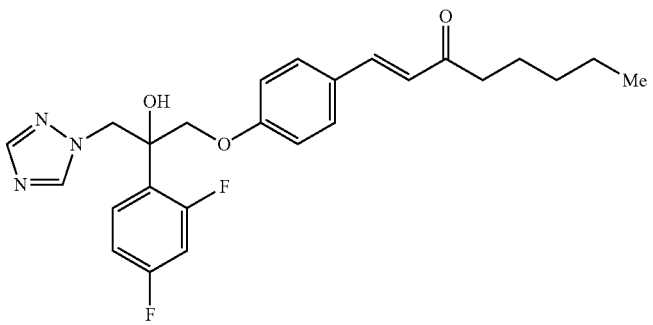<br>(E)-1-(4-(2-(2,4-Difluorophenyl)-2-hydroxy-3-(1H-1,2,4-triazol-1-yl)propoxy)phenyl)oct-1-en-1-one: | 28.3 | (200 MHz, CDCl₃): δ 0.91 (t, J = 6 Hz, 3H), 1.22-1.38 (m, 4H), 1.60-1.71 (m, 2H), 2.63 (t, J = 8 Hz, 2H), 4.26-4.32 (m, 2H), 4.65 (s, 1H), 4.80-4.96 (m, 2H), 6.63 (d, J = 16 Hz, 1H), 6.78-6.92 (m, 4H), 7.46-7.54 (m, 3H), 7.57-7.67 (m, 1H), 7.86 (s, 1H), 8.03 (s, 1H). |

TABLE 3-continued

| Compound No. | Compounds | Yield % | $^1$H NMR |
|---|---|---|---|
| 1A-27 | 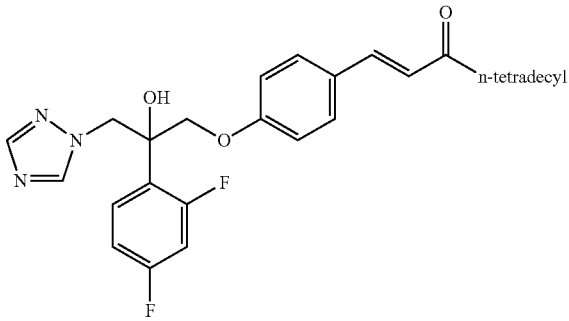<br>(E)-1-(4-(2-(2,4-Difluorophenyl)-2-hydroxy-3-(1H-1,2,4-triazol-1-yl)propoxy)phenyl)heptadec-1-en-3-one | 26.7 | (400 MHz, CDCl$_3$): δ 0.87 (t, J = 6 Hz, 3H), 1.19-1.30 (m, 22H), 1.61-1.66 (m, 2H), 2.61 (t, J = 6 Hz, 2H), 4.27 (s, 2H), 4.85 (s, 2H), 4.90 (bs, 1H), 6.63 (d, J = 16 Hz, 1H), 6.77-6.87 (m, 4H), 7.45-7.49 (m, 3H), 7.59-7.65 (m, 1H), 7.81 (s, 1H), 8.04 (s, 1H). |
| 1A-28 | 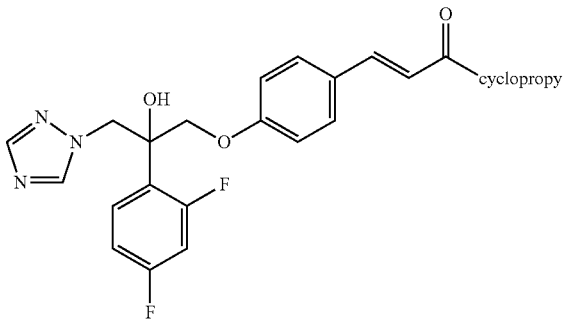<br>(E)-1-Cyclopropyl-3-(4-(2-(2,4-difluorophenyl)-2-hydroxy-3-(1H-1,2,4-triazol-1-yl)propoxy)phenyl)prop-2-en-1-one | 41.3 | (200 MHz, CDCl$_3$): δ 0.91-1.03 (m, 2H), 1.11-1.19 (m, 2H), 2.16-2.26 (m, 1H), 4.23-4.33 (m, 2H), 4.71 (s, 1H), 4.80-4.95 (m, 2H), 6.72-6.92 (m, 5H), 7.50 (d, J = 8 Hz, 2H), 7.57-7.69 (m, 2H), 7.85 (s, 1H), 8.04 (s, 1H). |
| 1A-29 | 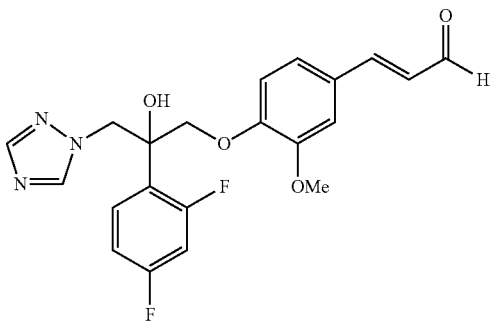<br>(E)-3-(4-(2-(2,4-Difluorophenyl)-2-hydroxy-3-(1H-1,2,4-triazol-1-yl)propoxy)-3-methoxyphenyl)acrylaldehyde | 48.5 | 67 (m, 1H), 7.82 (s, 1H), 8.06 (s, 1H), 9.67 (d, J = 8 Hz, 1H). |

Example 2

Preparation of 2,3-Dibromo-3-(2,4-dichlorophenyl)-1-(4-(2-(2,4-difluorophenyl)-2-hydroxy-3-(1H-1,2,4-triazol-1-yl)propoxy)phenyl)propan-1-one (1B-1)

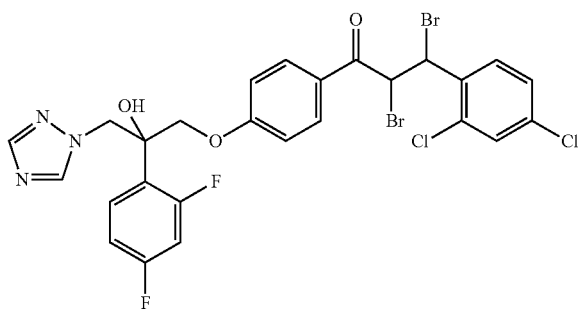 [SMILES: O=C(c1ccc(OCC(O)(Cn2cncn2)c2ccc(F)cc2F)cc1)C(Br)C(Br)c1ccc(Cl)cc1Cl]

To a solution of (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one (1A-7) (0.530 g, 1.0 mmol) in chloroform (10 ml), bromine (160 mg, 0.57 mL, 1.0 mmol) dissolved in chloroform (2 ml) was added slowly with stirring. After the completion of addition of bromine solution, the reaction mixture was stirred for 12 h. After completion of reaction, it was extracted with chloroform, dried over $Na_2SO_4$, concentrated and purified by column chromatography using pet ether-ethyl acetate (70:30) as eluent to give the pure product as 2,3-dibromo-3-(2,4-dichlorophenyl)-1-(4-(2-(2,4-difluorophenyl)-2-hydroxy-3-(1H-1,2,4-triazol-1-yl)propoxy)phenyl)propan-1-one of the Formula 1B-1 as off-white solid (561 mg, 81.1%). $^1$H NMR (200 MHz, $CDCl_3$): δ 4.35 (bs, 2H), 4.84-4.99 (m, 2H), 5.14 (bs, 1H), 5.80 (bs, 1H), 6.15 (bs, 1H), 6.75-6.89 (m, 2H), 6.96 (d, J=10 Hz, 2H), 7.33 (dd, J=8, 2 Hz, 1H), 7.42 (d, J=2 Hz, 1H), 7.52-7.68 (m, 2H), 7.86 (s, 1H), 8.03 (d, J=10 Hz, 2H), 8.36 (s, 1H).

Example 3

Preparation of (3-(2,4-dichlorophenyl)oxiran-2-yl)(4-(2-(2,4-difluorophenyl)-2-hydroxy-3-(1H-1,2,4-triazol-1-yl)propoxy)phenyl)methanone (1B-2)

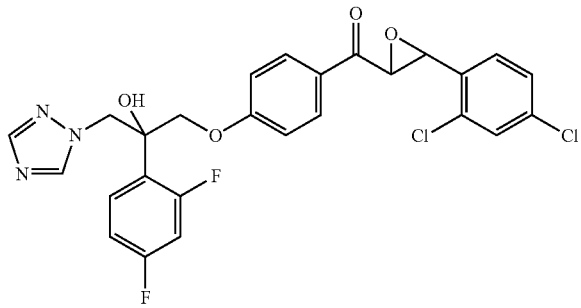 [SMILES: O=C(c1ccc(OCC(O)(Cn2cncn2)c2ccc(F)cc2F)cc1)C1OC1c1ccc(Cl)cc1Cl]

Powdered $K_2CO_3$ (0.414 g, 3 mmol) was added to a solution of (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one (Formula 1A-7) (0.530 g, 1.0 mmol) in MeOH (10 ml) at room temperature, followed by excess aqueous hydrogen peroxide (35%, 0.340 g, 10 mmol); added over 10 min. The mixture was stirred at room temperature for 3 h and reaction progress was monitored by TLC (70:30 EtOAc/Pet ether). Upon completion, the MeOH was removed under reduced pressure and the resulting residue was extracted with $CH_2Cl_2$, dried over $Na_2SO_4$, concentrated and purified by column chromatography using pet ether-ethyl acetate (60:40) as eluent to give the pure product (3-(2,4-dichlorophenyl)oxiran-2-yl)(4-(2-(2,4-difluorophenyl)-2-hydroxy-3-(1H-1,2,4-triazol-1-yl)propoxy)phenyl)methanone of Formula 1B-2 as pale yellow solid (482 mg, 88.4%). $^1$H NMR (200 MHz, $CDCl_3$): δ 4.08 (d, J=2 Hz, 1H), 4.29-4.33 (m, 3H), 4.80-4.96 (m, 3H), 6.75-6.91 (m, 2H), 6.95 (d, J=10 Hz, 2H), 7.15-7.44 (m, 3H), 7.57-7.70 (m, 1H), 7.85 (s, 1H), 8.01 (d, J=10 Hz, 2H), 8.04 (s, 1H).

Example 4

Preparation of (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-ol (1C-1)

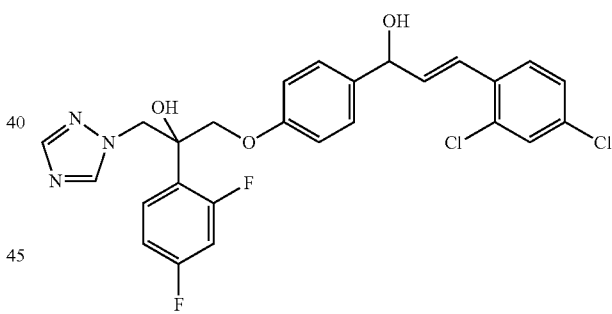

To a solution of (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one (Formula 1A-7) (500 mg, 0.943 mmol) in methanol (20 ml), was added sodium borohydride (35 mg, 0.943 mmol) at 0° C. and allowed to stir at room temperature for 3 h under nitrogen atmosphere. After completion of reaction, methanol was evaporated, extracted with ethyl acetate, dried over $Na_2SO_4$, concentrated and purified by column chromatography using pet ether-ethyl acetate (60:40) as eluent to give the pure product (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-ol of Formula 1C-1 as white fluffy solid (437 mg, 87.3%). $^1$H NMR (200 MHz, $CDCl_3$): δ 4.18-4.29 (m, 2H), 4.75 (bs, 1H), 4.83 (bs, 2H), 5.35 (d, J=6 Hz, 1H), 6.33 (dd, J=15, 6 Hz, 1H), 6.73-6.87 (m, 4H), 6.99 (d, J=15 Hz, 1H), 7.15 (dd, J=8, 2 Hz, 1H), 7.24-7.44 (m, 4H), 7.53-7.66 (m, 1H), 7.77 (s, 1H), 7.99 (s, 1H).

Example 5

Preparation of 1-(4-(5-(2,4-dichlorophenyl)-1H-pyrazol-3-yl)phenoxy)-2-(2,4-difluorophenyl)-3-(1H-1,2,4-triazol-1-yl)propan-2-ol (1D-1)

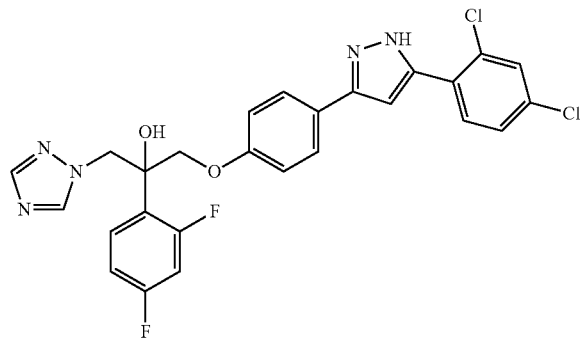 [SMILES: OC(COc1ccc(-c2cc(-c3ccc(Cl)cc3Cl)[nH]n2)cc1)(Cn1cncn1)c1ccc(F)cc1F]

The (3-(2,4-dichlorophenyl)oxiran-2-yl)(4-(2-(2,4-difluorophenyl)-2-hydroxy-3-(1H-1,2,4-triazol-1-yl)propoxy)phenyl)methanone (1B-2) (546 mg, 1.0 mmol) was dissolved in xylene (10 mL) and p-toluenesulfonic acid (95 mg, 0.5 mmol) and hydrazine hydrate (150 mg, 3.0 mmol) were added to the epoxide solution. The reaction mixture was stirred under refluxing conditions for 3 h until a yellow precipitate formed. The xylene was removed under reduced pressure, extracted with ethyl acetate, dried over Na₂SO₄, concentrated and purified by column chromatography using pet ether-ethyl acetate (70:30) as eluent to yield the pyrazole compound 1-(4-(5-(2,4-dichlorophenyl)-1H-pyrazol-3-yl)phenoxy)-2-(2,4-difluorophenyl)-3-(1H-1,2,4-triazol-1-yl)propan-2-ol of Formula 1D-1 as pale yellow solid (467 mg, 85.7%).

$^1$H NMR (200 MHz, CDCl$_3$): δ 4.19-4.30 (m, 2H), 4.87 (bs, 2H), 6.11 (bs, 2H), 6.76-6.90 (m, 5H), 7.16 (dd, J=10, 2 Hz, 1H), 7.42 (d, J=2 Hz, 1H), 7.52-7.75 (m, 4H), 7.85 (s, 1H), 8.02 (s, 1H).

Example 6

Preparation of 1-(4-(5-(2,4-dichlorophenyl)-4,5-dihydro-1H-pyrazol-3-yl)phenoxy)-2-(2,4-difluorophenyl)-3-(1H-1,2,4-triazol-1-yl)propan-2-ol (1E-1)

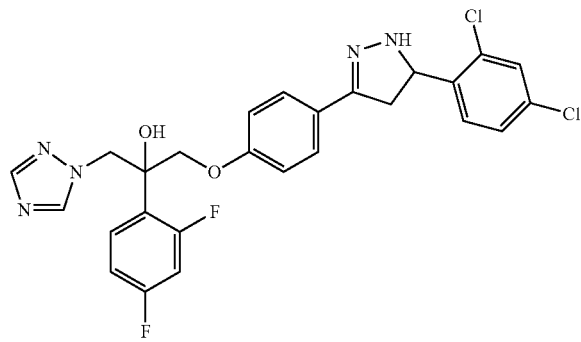 [SMILES: OC(COc1ccc(C2=NNC(c3ccc(Cl)cc3Cl)C2)cc1)(Cn1cncn1)c1ccc(F)cc1F]

A mixture of (E)-3-(2,4-Dichlorophenyl)-1-(4-(2-(2,4-difluorophenyl)-2-hydroxy-3-(1H-1,2,4-triazol-1-yl)propoxy)phenyl)prop-2-en-1-one (1A-7) (500 mg, 0.943 mmol), hydrazine hydrate (1.17 g, 23.5 mmol) and acetic acid (10 mL) was heated at reflux for 4 h, then poured onto crushed ice. The precipitate obtained was separated by filtration, washed with water, and crystallized from methanol to give pure compound 1-(4-(5-(2,4-dichlorophenyl)-4,5-dihydro-1H-pyrazol-3-yl)phenoxy)-2-(2,4-difluorophenyl)-3-(1H-1,2,4-triazol-1-yl)propan-2-ol of Formula 1E-1 as off-white solid (455 mg, 88.8%). $^1$H NMR (200 MHz, CDCl$_3$): δ 2.94 (dd, J=18, 4 Hz, 1H), 3.71 (dd, J=18, 12 Hz, 1H), 4.27 (s, 2H), 4.83 (s, 2H), 5.74 (dd, J=12, 4 Hz, 1H), 6.73-6.87 (m, 4H), 6.95 (d, J=8 Hz, 1H), 7.14 (dd, J=8, 2 Hz, 1H), 7.36 (d, J=2 Hz, 1H), 7.53-7.65 (m, 3H), 7.79 (s, 1H), 8.08 (s, 1H).

Example 7

Preparation of (E)-3-(2,4-dichlorophenyl)-1-(4-(2-(2,4-difluorophenyl)-2-methoxy-3-(1H-1,2,4-triazol-1-yl)propoxy)phenyl)prop-2-en-1-one (1A-19)

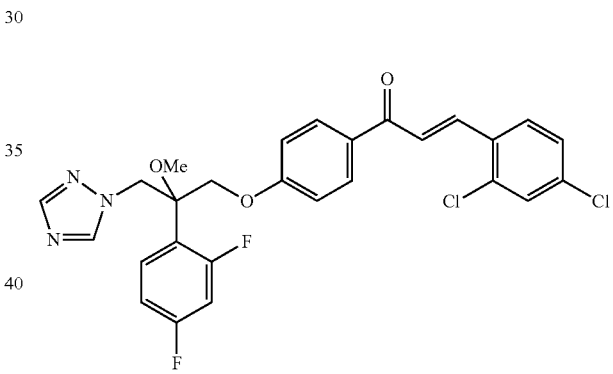

To a solution of (E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one (1A-7) (500 mg, 0.943 mmol) in dry DMF (20 ml), was added sodium hydride (37.7 mg, 0.943 mmol), followed by methyl iodide (0.10 mL, 1.69 mmol) at 0° C. and allowed to stir at room temperature for 8 h under nitrogen atmosphere. The reaction was quenched with ice-cold water, extracted with ethyl acetate, dried over Na₂SO₄, concentrated and purified by column chromatography using pet ether-ethyl acetate (70:30) as eluent to give the pure product (E)-3-(2,4-dichlorophenyl)-1-(4-(2-(2,4-difluorophenyl)-2-methoxy-3-(1H-1,2,4-triazol-1-yl)propoxy)phenyl)prop-2-en-1-one of Formula 1A-19 as yellow fluffy solid (454 mg, 88.7%). $^1$H NMR (500 MHz, CDCl$_3$): δ 3.34 (s, 3H), 4.45 (d, J=10 Hz, 1H), 4.50 (d, J=10 Hz, 1H), 4.62 (d, J=15 Hz, 1H), 4.73 (d, J=15 Hz, 1H), 6.76-6.85 (m, 2H), 6.94 (d, J=10 Hz, 2H), 7.20 (dd, J=10, 2

Hz, 1H), 7.24-7.29 (m, 1H), 7.34 (d, J=2 Hz, 1H), 7.41 (d, J=15 Hz, 1H), 7.61 (d, J=5 Hz, 1H), 7.73 (s, 1H), 7.95 (d, J=10 Hz, 1H), 7.96 (s, 1H), 8.00 (d, J=15 Hz, 1H).

Example 8

(E)-1-(4-(2-(Allyloxy)-2-(2,4-difluorophenyl)-3-(1H-1,2,4-triazol-1-yl)propoxy)phenyl)-3-(2,4-dichlorophenyl)prop-2-en-1-one (1A-18)

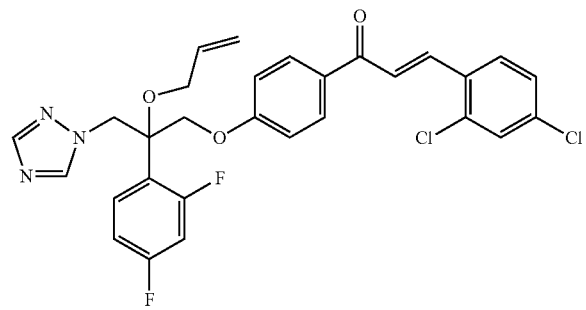 [SMILES: C=CCOC(COc1ccc(C(=O)/C=C/c2ccc(Cl)cc2Cl)cc1)(Cn1cncn1)c1ccc(F)cc1F]

The same procedure described above for Formula 1A-19 was used for the preparation of compound of Formula 1A-18 using allyl bromide instead of methyl iodide. Yield: 85.6%; $^1$H NMR (200 MHz, CDCl$_3$): δ 4.09 (d, J=4 Hz, 2H), 4.47 (dd, J=10, 2 Hz, 1H), 4.61 (d, J=10 Hz, 1H), 4.67 (d, J=14 Hz, 1H), 4.81 (d, J=14 Hz, 1H), 5.19-5.37 (m, 2H), 5.84-6.03 (m, 1H), 6.81-6.96 (m, 2H), 6.99 (d, J=8 Hz, 2H), 7.28-7.39 (m, 2H), 7.45 (d, J=8 Hz, 1H), 7.49 (d, J=7 Hz, 1H), 7.69 (d, J=8 Hz, 1H), 7.82 (s, 1H), 8.03 (d, J=8 Hz, 2H), 8.07 (s, 1H), 8.14 (s, 1H).

Example 9

Preparation of S-(+)-(E)-3-(4-chlorophenyl)-1-(4-(2-(2,4-difluorophenyl)-2-hydroxy-3-(1H-1,2,4-triazol-1-yl)propoxy)phenyl)prop-2-en-1-one (Formula S-(+)-1A-6)

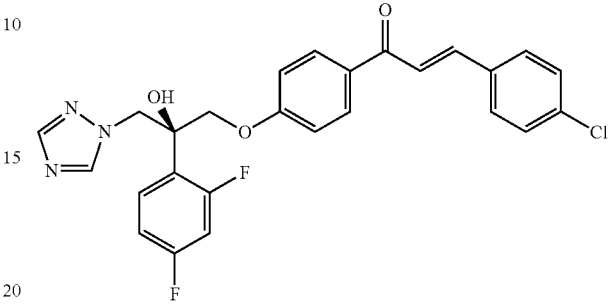

To the flame dried K$_2$CO$_3$ (262 mg, 1.9 mmol), were added (E)-3-(4-chlorophenyl)-1-(4-hydroxyphenyl)prop-2-en-1-one (232 mg, 0.91 mmol), tetra-butyl ammonium bromide (TBAB, 246 mg) and S-(−)-1-[2-(2,4-difluorophenyl)-oxiranylmethyl]-1H-[1,2,4]triazole (180 mg, 0.76 mmol) dissolved in dry ethyl acetate (15 mL). The reaction mixture was allowed to stir under reflux for 12 h under nitrogen atmosphere. It was then cooled to room temperature, diluted with water, extracted with ethyl acetate, dried over Na$_2$SO$_4$, concentrated and purified by column chromatography using pet ether-ethyl acetate (40:60) as eluent to give pure compound of Formula S-(+)-1A-6 (240 mg, 64.3%). [α]$_D$+ 11.91° (c=1, THF). Chiral HPLC using Chiralcel OD-H (250×4.6 mm) column using 25% ethanol in pet ether as mobile phase showed the product to have RT 31.817 min and 77.9% ee.

The following compounds given herein below in Table 4 were prepared using above procedure by reaction of various hydroxyl chalcones with suitable epoxides:

TABLE 4

| Compound Nos. | Compounds | [α]$_D$ | HPLC conditions | RT (min) | ee (%) |
|---|---|---|---|---|---|
| R-(−)-1A-2 | | −11.28° | Chiralcel OD-H (250 × 4.6 mm), ethanol - pet ether (25:75), 254 nm | 32.800 | 71.8 |

R-(−)-(E)-1-(4-(2-(2,4-Difluorophenyl)-2-hydroxy-3-(1H-1,2,4-triazol-1-yl)propoxy)phenyl)-3-(4-methoxyphenyl)prop-2-en-1-one TABLE 4-continued

| Compound Nos. | Compounds | $[\alpha]_D$ | HPLC conditions | RT (min) | ee (%) |
|---|---|---|---|---|---|
| S-(+)-1A-2 | S-(+)-(E)-1-(4-(2-(2,4-Difluorophenyl)-2-hydroxy-3-(1H-1,2,4-triazol-1-yl)propoxy)phenyl)-3-(4-methoxyphenyl)prop-2-en-1-one | +13.80° | Chiralcel OD-H (250 × 4.6 mm), ethanol - pet ether (25:75), 254 nm | 40.767 | 95.2 |
| S-(+)-1A-13 | S-(+)-(E)-1-(4-(2-(2,4-Difluorophenyl)-2-hydroxy-3-(1H-1,2,4-triazol-1-yl)propoxy)phenyl)-3-(thiophen-2-yl)prop-2-en-1-one | +13.59° | Chiralcel OD-H (250 × 4.6 mm), iso-propanol - pet ether (40:60), 254 nm | 28.317 | 94.7 |
| R-(−)-1A-13 | R-(−)-(E)-1-(4-(2-(2,4-Difluorophenyl)-2-hydroxy-3-(1H-1,2,4-triazol-1-yl)propoxy)phenyl)-3-(thiophen-2-yl)prop-2-en-1-one | −11.98° | Chiralcel OD-H (250 × 4.6 mm), iso-propanol - pet ether (40:60), 254 nm | 41.567 | 94.2 |

Example 10

Preparation of R-(−)-(E)-3-(4-chlorophenyl)-1-(4-(2-(2,4-difluorophenyl)-2-hydroxy-3-(1H-1,2,4-triazol-1-yl)propoxy)phenyl)prop-2-en-1-one (Formula R-(−)-1A-6)

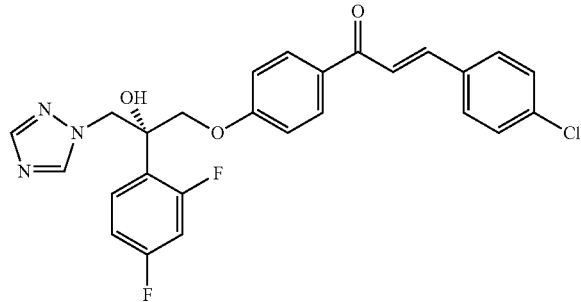 [SMILES: O=C(/C=C/c1ccc(Cl)cc1)c1ccc(OC[C@](O)(Cn2cncn2)c2ccc(F)cc2F)cc1]

Racemic 1A-6 was resolved by preparative chiral HPLC using Chiralcel OD (16×100 mm) column and pet ether-ethanol (75:25) as eluent. The enantiomer that eluted out first was found to be R-(−)-(E)-3-(4-chlorophenyl)-1-(4-(2-(2,4-difluorophenyl)-2-hydroxy-3-(1H-1,2,4-triazol-1-yl) propoxy)phenyl)prop-2-en-1-one (Formula R-(−)-1A-6) with $[\alpha]_D$ −12.30°(c=1.1, THF). Chiral HPLC using Chiralcel OD-H (250×4.6 mm) column using 25% ethanol in pet ether as mobile phase showed the product to have 97.8% ee.

Example 11

Antifungal Activity Testing

The compounds of Formula 1 were tested for antifungal activity against *Candida albicans*, *Aspergillus niger* and *Fusarium proliferatum*. In vitro evaluation of antifungal activity was performed by determining the minimum inhibitory concentration (MIC) following standard methods (CLSI: Reference method for broth dilution antifungal susceptibility testing of yeasts; Approved standard, second edition M27-A2, 2002; CLSI: Reference method for broth dilution antifungal susceptibility testing of filamentous fungi; Approved standard M38-A, 2002). Anti-fungal susceptibility testing of these anti-fungal compounds was done by broth dilution method using RPMI 1640 medium with MOPS buffer. Known anti-fungal agents like fluconazole and amphotericin-B were used as positive control. End points were determined after 48 hours visually and by using spectrophotometer wherever necessary. Different dilutions were tried and various sets of experiments performed. The activity parameters are enumerated in Table 5.

TABLE 5

| Sr no | Comp no | Activity against organisms ($MIC_{50}$ in μg/ml)* | | | | | | | | |
|---|---|---|---|---|---|---|---|---|---|---|
| | | Ca01 A[$] | Ca01 B[$] | Cg01 | Ck01 | Ct01 | Cn01 | An01 | Afm01 | Fp01 |
| 1 | FLU | 1 | 0.25 | 1 | 32 | 1 | 2 | >128 | >128 | >128 |
| 2 | AMB | 0.25 | 0.25 | 0.25 | 0.5 | 0.5 | 0.5 | 0.25 | 0.5 | 2 |
| 3 | 1A-1 | 0.12 | 0.06 | 0.25 | >2 | 0.5 | 1 | >2 | >2 | >2 |
| 4 | 1A-2 | 0.12 | 0.06 | 0.25 | 4 | 0.25 | 1 | 4 | >4 | >4 |
| 5 | 1A-3 | 0.5 | 0.25 | 0.5 | >8 | 2 | 8 | >8 | >8 | >8 |
| 6 | 1A-4 | 1 | 0.25 | 2 | >4 | 2 | 2 | >4 | >4 | >4 |
| 7 | 1A-5 | 1 | 0.25 | 1 | >4 | 1 | >4 | >4 | >4 | >4 |
| 8 | 1A-6 | 0.25 | 0.5 | 0.5 | 2 | 0.5 | 0.5 | >4 | >4 | >4 |
| 9 | 1A-7 | 0.25 | 0.25 | 0.5 | 2 | 1 | 2 | >4 | >4 | >4 |
| 10 | 1A-8 | 0.12 | 0.12 | 0.25 | 4 | 0.5 | 2 | >4 | >4 | >4 |
| 11 | 1A-9 | >2 | >2 | >2 | >2 | >2 | >2 | >2 | >2 | >2 |
| 12 | 1A-10 | 2 | 0.25 | 0.5 | 4 | 4 | 0.5 | >4 | >4 | >4 |
| 13 | 1A-11 | 1 | 0.5 | 1 | >4 | >4 | 1 | >4 | >4 | >4 |
| 14 | 1A-12 | 2 | 0.5 | 0.5 | 4 | 4 | 0.5 | >4 | >4 | >4 |
| 15 | 1A-13 | 0.25 | 0.12 | 0.25 | 8 | 0.5 | 1 | >8 | >8 | >8 |
| 16 | 1A-14 | 0.5 | 0.25 | 0.5 | 1 | 0.5 | 0.5 | >4 | >4 | >4 |
| 17 | 1A-15 | >2 | >2 | 2 | >2 | >2 | 2 | >2 | >2 | >2 |
| 18 | 1A-16 | 0.5 | 0.25 | 2 | >4 | 2 | 4 | >4 | >4 | >4 |
| 19 | 1A-17 | 0.5 | 0.25 | 0.25 | 8 | 2 | 1 | >8 | >8 | >8 |
| 20 | 1A-18 | >4 | >4 | >4 | >4 | >4 | >4 | >4 | >4 | >4 |
| 21 | 1A-19 | >4 | 1 | 1 | >4 | >4 | >4 | >4 | >4 | >4 |
| 22 | 1B-1 | 0.5 | 0.25 | 0.5 | 2 | 1 | 0.5 | >8 | >8 | >8 |
| 23 | 1C-1 | 0.5 | 0.5 | 0.25 | 4 | 1 | 0.5 | >4 | >4 | >4 |
| 24 | 1B-2 | 0.5 | 0.5 | 0.5 | 4 | 1 | 1 | >4 | >4 | >4 |
| 25 | 1D-1 | 0.5 | 0.5 | 1 | 2 | 0.5 | 1 | >4 | >4 | >4 |
| 26 | 1E-1 | 0.25 | 0.25 | 2 | >8 | 1 | 2 | >8 | >8 | >8 |
| 27 | 1A-20 | 0.25 | 0.12 | 0.25 | 4 | 1 | 1 | >4 | 8 | >4 |
| 28 | 1A-21 | 0.25 | 0.12 | 0.25 | 2 | 1 | 1 | >4 | 8 | >4 |
| 29 | 1A-22 | 0.25 | 0.12 | 0.5 | 2 | 1 | 1 | >4 | >4 | >4 |
| 30 | 1A-23 | 0.5 | 0.5 | 1 | 2 | 0.5 | 1 | >4 | >4 | >4 |
| 31 | 1A-24 | 8 | 4 | 0.12 | >4 | >4 | >4 | >4 | >4 | >4 |
| 32 | 1A-25 | 0.25 | 0.12 | 0.12 | 8 | 2 | 4 | 8 | 8 | >128 |
| 33 | 1A-26 | 0.25 | 0.12 | 0.06 | 1 | 2 | 0.5 | >4 | >4 | >4 |
| 34 | 1A-27 | >1 | >1 | >1 | >1 | >1 | >1 | >1 | >1 | >1 |
| 35 | 1A-28 | 0.06 | 0.015 | 0.03 | 1 | 0.25 | 2 | 8 | 16 | >16 |
| 36 | 1A-29 | 0.5 | 0.25 | 1 | 32 | 8 | 16 | >64 | >64 | >64 |
| 37 | S-(+)-1A-6 | 2 | 1 | 0.5 | 4 | 2 | 2 | >4 | >4 | >4 |
| 38 | R-(−)-1A-6 | 0.12 | 0.06 | 0.12 | 1 | 0.5 | 0.25 | >4 | >4 | >4 |
| 39 | R-(−)-1A-2 | 0.12 | 0.06 | 0.06 | 2 | 0.25 | 0.5 | 2 | >4 | >4 |
| 40 | S-(+)-1A-2 | 1 | 0.5 | 1 | >4 | 2 | 2 | >4 | >4 | >4 |

TABLE 5-continued

| | Activity against organisms ($MIC_{50}$ in µg/ml)* | | | | | | | | |
|---|---|---|---|---|---|---|---|---|---|
| Sr no | Comp no | Ca01 A$ | Ca01 B$ | Cg01 | Ck01 | Ct01 | Cn01 | An01 | Afm01 | Fp01 |
| 41 | S-(+)-1A-13 | 0.5 | 0.25 | 0.25 | >4 | 2 | 4 | >4 | >4 | >4 |
| 42 | R-(−)-1A-13 | 0.12 | 0.03 | 0.03 | 2 | 0.12 | 0.5 | >4 | >4 | >4 |

$A: $MIC_{80}$ in µg/ml; B: $MIC_{50}$ in µg/ml
Ca01: *C. albicans* ATCC 24433; Cg01: *C. glabrata* ATCC 90030; Ck01: *C. krusei* ATCC 6258; Ct01: *C. tropicalis* ATCC 750; Cn01: *C. neoformans* ATCC 34664; Afm01: *A. fumigatus* ATCC 46645; An01: *A. niger* ATCC 16404; Fp01: *F. proliferatum* ATCC 10052.
*For azoles: For Fluconazole and the NCEs, MIC is recorded as the concentration exhibiting 80% inhibition as compared to the positive control.
For Amphotericin B: MIC is recorded as the concentration exhibiting complete inhibition.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. An antifungal compound of Formula (1), an (R) enantiomer thereof, an (S) enantiomer thereof, a racemate thereof, or a pharmaceutically acceptable salt thereof:

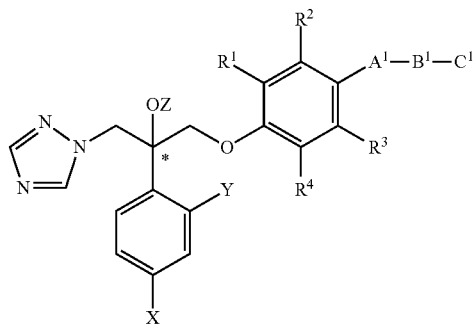

Formula 1 wherein:
X and Y are independently selected from the group consisting of hydrogen, fluorine, chlorine and bromine;
Z is selected from the group consisting of hydrogen, alkyl, alkenyl, and acyl;
$R^1$, $R^2$, $R^3$ and $R^4$ are independently selected from the group consisting of:
hydrogen;
a linear or branched alkyl group having 1 to 20 carbon atoms;
an alkoxy group having 1 to 4 carbon atoms;
a hydroxyl group,
a halogen selected from the group consisting of fluorine, chlorine, bromine and iodine; and
a nitro group;
$A^1$ and $B^1$ are independently selected from the group consisting of:
—C=O;
—CH=CH—;
alkyl;
brominated alkyl;
cycloalkyl;
aziridinyl;
an epoxy ring;
—CH($OR^5$), wherein $R^5$ is H, alkyl or acyl;
—C=N—$OR^6$ wherein $R^6$ is H or alkyl;
—C=N—$R^7$ wherein $R^7$ is alkyl or aryl; and
—C=N—$R^7$ wherein $R^7$ is alkyl; and
—C($X'R^8$)$Y'R^9$ wherein X' and Y' are independently selected from the group consisting of O and S, and $R^8$ and $R^9$ are (a) independently selected from alkyl, or (b) linked with each other to form a heterocyclic five to eight-membered ring; or
$A^1$-$B^1$ is a heterocyclic ring selected from the group consisting of 3,5-disubstituted (1H)-pyrazole or 3,5-disubstituted 4,5-dihydro(1H)-pyrazole;
$C^1$ is selected from the group consisting of hydrogen; phenyl, optionally substituted with at least one group selected from the group consisting of an alkyl group, an alkoxy group, fluorine, and bromine; heteroaryl; thienyl; naphthyl; anthracenyl; indolyl; cycloalkyl; and an alkyl group; and
'*' represents a chiral carbon atom.

2. An antifungal compound of Formula (1), an (R) enantiomer thereof, an (S) enantiomer thereof, a racemate thereof, or a pharmaceutically acceptable salt thereof:

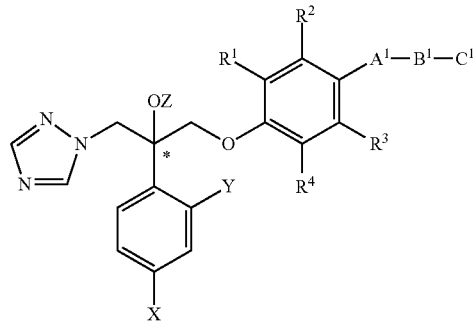

Formula 1 wherein:
X and Y are independently selected from the group consisting of hydrogen, fluorine, chlorine and bromine;
Z is selected from the group consisting of hydrogen, alkyl, alkenyl, and acyl;
$R^1$, $R^2$, $R^3$ and $R^4$ are independently selected from the group consisting of hydrogen and an alkoxy group having 1 to 4 carbon atoms;

C¹ is selected from the group consisting of hydrogen; phenyl, optionally substituted with at least one group selected from the group consisting of an alkyl group, an alkoxy group, fluorine, and bromine; thienyl; naphthyl; anthracenyl; indolyl; N-methylindolyl; cycloalkyl; and an alkyl group; and '*' represents a chiral carbon atom, wherein said antifungal compound of Formula (1) is:
(i) Compound 1A, wherein Compound 1A is a compound of Formula (1) wherein either:
A¹ is —C=O and B¹ is —CH=CH—, or
A¹ is —CH=CH— and B¹ is —C=O;
(ii) Compound 1B, wherein Compound 1B is a compound of Formula (1), wherein either:
A¹ is —C=O, and B¹ is alkyl or an epoxy ring; or
A¹ is alkyl or an epoxy ring, and B¹ is —C=O;
(iii) Compound 1C, wherein Compound 1C is a compound of Formula (1), wherein either:
A¹ is —CH=CH—, and B¹ is —CH(OR⁵); or
A¹ is —CH(OR⁵), and B¹ is —CH=CH—;
(iv) Compound 1D, wherein Compound 1D is a compound of Formula (1), wherein A¹-B¹ is a 3,5-disubstituted (1H)-pyrazole; or
(v) Compound 1E, wherein Compound 1E is a compound of Formula (1), wherein A¹-B¹ is a 3,5-disubstituted 4,5-dihydro(1H)-pyrazole.

3. The antifungal compound of Formula (1) as claimed in claim 2, wherein said antifungal compound of Formula (1) is Compound 1A, wherein Compound 1A is a compound of Formula (1) wherein either A¹ is —C=O and B¹ is —CH=CH—, or A¹ is —CH=CH— and B¹ is —C=O.

4. The antifungal compound of Formula (1) as claimed in claim 1, wherein said antifungal compound of Formula (1) is Compound 1B, wherein Compound 1B is a compound of Formula (1), wherein either:
A¹ is —C=O, and B¹ is alkyl, brominated alkyl or an epoxy ring; or A¹ is alkyl, brominated alkyl or an epoxy ring, and B¹ is —C=O.

5. The antifungal compound of Formula (1) as claimed in claim 1, wherein said antifungal compound of Formula (1) is Compound 1C, wherein Compound 1C is a compound of Formula (1), wherein either A¹ is —CH=CH—, and B¹ is —CH(OR⁵), —C=N—OR⁶, —C=N—R⁷ or —C(X'R⁸)Y'R⁹; or A¹ is —CH(OR⁵), —C=N—OR⁶, —C=N—R⁷ or —C(X'R⁸)Y'R⁹, and B¹ is —CH=CH—.

6. The antifungal compound of Formula (1) as claimed in claim 2, wherein said antifungal compound of Formula (1) is Compound 1D, wherein Compound 1D is a compound of Formula (1), wherein A¹-B¹ is a 3,5-disubstituted (1H)-pyrazole.

7. The antifungal compound of Formula (1) as claimed in claim 2, wherein said antifungal compound of Formula (1) is Compound 1E, wherein Compound 1E is a compound of Formula (1), wherein A¹-B¹ is a 3,5-disubstituted 4,5-dihydro(1H)-pyrazole.

8. An antifungal compound selected from the group consisting of:

(E)-1-(4-(2-(2,4-Difluorophenyl)-2-hydroxy-3-(1H-1,2,4-triazol-1-yl)propoxy) phenyl)-3-phenylprop-2-en-1-one;

(E)-1-(4-(2-(2,4-Difluorophenyl)-2-hydroxy-3-(1H-1,2,4-triazol-1-l)propoxy)phenyl)-3-(4-methoxyphenyl)prop-2-en-1-one;

(E)-1-(4-(2-(2,4-Difluorophenyl)-2-hydroxy-3-(1H-1,2,4-triazol-1-l)propoxy)phenyl)-3-(2-methoxyphenyl)prop-2-en-1-one;

(E)-1-(4-(2-(2,4-Difluorophenyl)-2-hydroxy-3-(1H-1,2,4-triazol-1-l)propoxy)phenyl)-3-(3,5-dimethoxyphenyl)prop-2-en-1-one;

(E)-1-(4-(2-(2,4-Difluorophenyl)-2-hydroxy-3-(1H-1,2,4-triazol-1-l)propoxy)phenyl)-3-(3,4,5-trimethoxyphenyl)prop-2-en-1-one;

(E)-3-(4-Chlorophenyl)-1-(4-(2-(2,4-difluorophenyl)-2-hydroxy-3-(1H-1,2,4-triazol-1-yl)propoxy)phenyl)prop-2-en-1-one;

(E)-3-(2,4-dichlorophenyl)-1-(4-(2-(2,4-difluorophenyl)-2-hydroxy-3-(1H-1,2,4-triazol-1-yl)propoxy)phenyl)prop-2-en-1-one;

(E)-1-(4-(2-(2,4-Difluorophenyl)-2-hydroxy-3-(1H-1,2,4-triazol-1-yl)propoxy) phenyl)-3-(2-fluorophenyl)prop-2-en-1-one;

(E)-1-(4-(2-(2,4-Difluorophenyl)-2-hydroxy-3-(1H-1,2,4-triazol-1-yl)propoxy) phenyl)-3-(4-(octyloxy)phenyl)prop-2-en-1-one;

(E)-1-(4-(2-(4-Fluorophenyl)-2-hydroxy-3-(1H-1,2,4-triazol-1-yl)propoxy)phenyl)-3-(4-methoxyphenyl)prop-2-en-1-one;

(E)-1-(4-(2-(4-Bromophenyl)-2-hydroxy-3-(1H-1,2,4-triazol-1-yl)propoxy)phenyl)-3-(4-methoxyphenyl)prop-2-en-1-one;

(E)-3-(4-Chlorophenyl)-1-(4-(2-(4-fluorophenyl)-2-hydroxy-3-(1H-1,2,4-triazol-1-yl)propoxy)phenyl)prop-2-en-1-one;

(E)-1-(4-(2-(2,4-Difluorophenyl)-2-hydroxy-3-(1H-1,2,4-triazol-1-yl)propoxy) phenyl)-3-(thiophen-2-yl)prop-2-en-1-one;

(E)-1-(4-(2-(2,4-Difluorophenyl)-2-hydroxy-3-(1H-1,2,4-triazol-1-yl)propoxy) phenyl)-3-(naphthalen-2-yl)prop-2-en-1-one;

(E)-3-(Anthracen-9-yl)-1-(4-(2-(2,4-difluorophenyl)-2-hydroxy-3-(1H-1,2,4-triazol-1-yl)propoxy)phenyl)prop-2-en-1-one;

(E)-1-(4-(2-(2,4-Difluorophenyl)-2-hydroxy-3-(1H-1,2,4-triazol-1-yl)propoxy) phenyl)-3-(1-methyl-1H-indol-3-yl)prop-2-en-1-one;

(E)-1-(4-(2-(4-Fluorophenyl)-2-hydroxy-3-(1H-1,2,4-triazol-1-yl)propoxy)phenyl)-3-(thiophen-2-yl)prop-2-en-1-one;

(E)-3-(4-(2-(2,4-Difluorophenyl)-2-hydroxy-3-(1H-1,2,4-triazol-1-yl)propoxy) phenyl)-1-(4-methoxyphenyl)prop-2-en-1-one;

(E)-3-(4-(2-(2,4-Difluorophenyl)-2-hydroxy-3-(1H-1,2,4-triazol-1-yl)propoxy) phenyl)-1-(p-tolyl)prop-2-en-1-one;

(E)-1-(2,4-Dichlorophenyl)-3-(4-(2-(2,4-difluorophenyl)-2-hydroxy-3-(1H-1,2,4-triazol-1-yl)propoxy)phenyl)prop-2-en-1-one;

(E)-3-(4-(2-(2,4-Difluorophenyl)-2-hydroxy-3-(1H-1,2,4-triazol-1-yl)propoxy)-3-methoxyphenyl)-1-(4-methoxyphenyl)prop-2-en-1-one;

(E)-3-(4-(2-(2,4-Difluorophenyl)-2-hydroxy-3-(1H-1,2,4-triazol-1-yl)propoxy) phenyl)-1-(4-(octyloxy)phenyl)prop-2-en-1-one;

(E)-4-(4-(2-(2,4-Difluorophenyl)-2-hydroxy-3-(1H-1,2,4-triazol-1-yl)propoxy) phenyl) but-3-en-2-one;

(E)-1-(4-(2-(2,4-Difluorophenyl)-2-hydroxy-3-(1H-1,2,4-triazol-1-yl)propoxy)phenyl)oct-1-en-3-one;

(E)-1-(4-(2-(2,4-Difluorophenyl)-2-hydroxy-3-(1H-1,2,4-triazol-1-yl)propoxy) phenyl)heptadec-1-en-3-one;

(E)-1-Cyclopropyl-3-(4-(2-(2,4-difluorophenyl)-2-hydroxy-3-(1H-1,2,4-triazol-1-yl) propoxy)phenyl)prop-2-en-1-one;

(E)-3-(4-(2-(2,4-Difluorophenyl)-2-hydroxy-3-(1H-1,2,4-triazol-1-yl)propoxy)-3-methoxyphenyl)acrylaldehyde;

2,3-Dibromo-3-(2,4-dichlorophenyl)-1-(4-(2-(2,4-difluorophenyl)-2-hydroxy-3-(1H-1,2,4-triazol-1-yl)propoxy)phenyl)propan-1-one;

(3-(2,4-Dichlorophenyl) oxiran-2-yl) (4-(2-(2,4-difluorophenyl)-2-hydroxy-3-(1H-1,2,4-triazol-1-yl)propoxy)phenyl) methanone;

(E)-3-(2,4-Dichlorophenyl)-1-(4-(2-(2,4-difluorophenyl)-2-hydroxy-3-(1H-1,2,4-triazol-1-yl)propoxy)phenyl) prop-2-en-1-ol;

1-(4-(5-(2,4-Dichlorophenyl)-1H-pyrazol-3-yl)phenoxy)-2-(2,4-difluorophenyl)-3-(1H-1,2,4-triazol-1-yl)propan-2-ol;

1-(4-(5-(2,4-Dichlorophenyl)-4,5-dihydro-1H-pyrazol-3-yl)phenoxy)-2-(2,4-difluorophenyl)-3-(1H-1,2,4-triazol-1-yl)propan-2-ol;

(E)-3-(2,4-dichlorophenyl)-1-(4-(2-(2,4-difluorophenyl)-2-methoxy-3-(1H-1,2,4-triazol-1-yl)propoxy)phenyl) prop-2-en-1-one;

(E)-1-(4-(2-(Allyloxy)-2-(2,4-difluorophenyl)-3-(1H-1,2,4-triazol-1-yl)propoxy) phenyl)-3-(2,4-dichlorophenyl)prop-2-en-1-one;

S-(+)-(E)-3-(4-chlorophenyl)-1-(4-(2-(2,4-difluorophenyl)-2-hydroxy-3-(1H-1,2,4-triazol-1-yl)propoxy)phenyl)prop-2-en-1-one;

R-(−)-(E)-1-(4-(2-(2,4-Difluorophenyl)-2-hydroxy-3-(1H-1,2,4-triazol-1-yl) propoxy) phenyl)-3-(4-methoxyphenyl)prop-2-en-1-one;

S-(+)-(E)-1-(4-(2-(2,4-Difluorophenyl)-2-hydroxy-3-(1H-1,2,4-triazol-1-yl) propoxy) phenyl)-3-(4-methoxyphenyl)prop-2-en-1-one;

S-(+)-(E)-1-(4-(2-(2,4-Difluorophenyl)-2-hydroxy-3-(1H-1,2,4-triazol-1-yl) propoxy) phenyl)-3-(thiophen-2-yl)prop-2-en-1-one;

R-(−)-(E)-1-(4-(2-(2,4-Difluorophenyl)-2-hydroxy-3-(1H-1,2,4-triazol-1-yl) propoxy) phenyl)-3-(thiophen-2-yl)prop-2-en-1-one.

9. A method of making the antifungal compound of Formula (1) as claimed in claim 2, wherein said antifungal compound is Compound 1A, Z is H, and either (a) $A^1$ is —C=O and $B^1$ is —CH=CH— or (b) $A^1$ is —CH=CH— and $B^1$ is —C=O, said method comprising:
(i) reacting an epoxide of Formula 2 with a compound of Formula 3 in presence of a base and an optional phase transfer catalyst to obtain a compound of Formula 4:

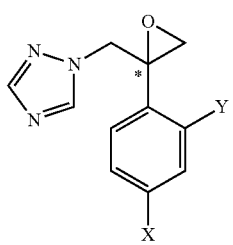

Formula 2

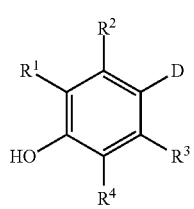

Formula 3

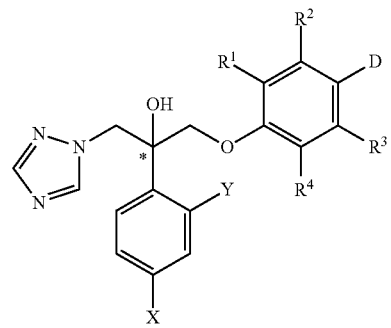

Formula 4 wherein $R^1$, $R^2$, $R^3$, $R^4$, X, Y and '*' are as defined in claim 2, and D represents —CHO or —COCH$_3$, and
(ii) reacting the compound of Formula 4 with an aldehyde or ketone in the presence of a base.

10. The method as claimed in claim 9, wherein:
the base in step (i) is selected from the group consisting of potassium carbonate, sodium carbonate, cesium carbonate and lithium carbonate, and
the phase transfer catalyst in step (i) is selected from the group consisting of tetra-n-butylammonium bromide (TBAB), tetra-n-butylammonium chloride, benzyltriethylammonium bromide, benzyltriethylammonium chloride, cetyltri-n-butylphosphonium bromide, cetyltrimethylammonium bromide, and cetyltrimethylammonium chloride.

11. The method as claimed in claim 9, wherein:
the base in step (ii) is selected from the group consisting of sodium hydroxide, potassium hydroxide, lithium hydroxide, sodium methoxide, and potassium tert butoxide.

12. The method as claimed in claim 9, wherein step (ii) comprises:
(ii) reacting the compound of Formula 4 with an aldehyde in the presence of a base, where the aldehyde is selected from the group consisting of aliphatic, aromatic, and heteroaromatic aldehydes.

13. The method as claimed in claim 9, wherein step (ii) comprises:
(ii) reacting the compound of Formula 4 with a ketone in the presence of a base, where the ketone is selected from the group consisting of aliphatic, aromatic, and heteroaromatic ketones.

14. A method of making the antifungal compound of Formula (1) as claimed in claim 2, wherein said antifungal compound is Compound 1A, Z is H, and either (a) $A^1$ is —C=O and $B^1$ is —CH=CH— or (b) $A^1$ is —CH=CH— and $B^1$ is —C=O, said method comprising:
reacting a compound of Formula 2 with a substituted enone of Formula 5, in the presence of a base and an optional phase transfer catalyst:

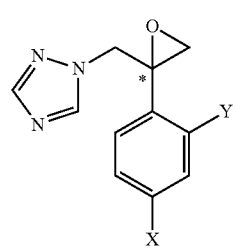

Formula 2

-continued

Formula 5

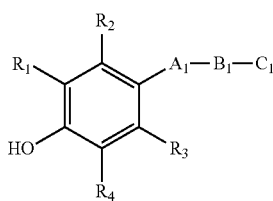

wherein $R^1$, $R^2$, $R^3$, $R^4$, X, Y, $C^1$ and '*' are as defined in claim 2.

15. A method as claimed in claim 14, wherein:
the base is selected from the group consisting of potassium carbonate, sodium carbonate, cesium carbonate and lithium carbonate, and
the phase transfer catalyst is selected from the group consisting of tetra-n-butylammonium bromide (TBAB), tetra-n-butylammonium chloride, benzyltriethylammonium bromide, benzyltriethylammonium chloride, cetyltri-n-butylphosphonium bromide, cetyltrimethylammonium bromide, and cetyltrimethylammonium chloride.

16. A method of making the antifungal compound of Formula (1) as claimed in claim 1, wherein Z is selected from the group consisting of alkyl, alkenyl, and acyl; said method comprising:
reacting a reactant of formula (1), wherein Z is H, with a compound of formula Z'—X, wherein:
Z' is alkyl, alkenyl, and acyl, and X is a halogen selected from iodine, bromine or chlorine.

17. A method of making the antifungal compound of Formula (1) as claimed in claim 2, wherein the antifungal compound is Compound 1B,
wherein said method comprises halogenation, epoxidation, or reduction of an unsaturated double bond in Compound 1A.

18. A method of making the antifungal compound of Formula (1) as claimed in claim 2, wherein the antifungal compound is Compound 1C,
wherein said method comprises reduction, oximation, or ketalization of a carbonyl group in Compound 1A.

19. A method of making the antifungal compound of Formula (1) as claimed in claim 2, wherein the antifungal compound is Compound 1D,
said method comprising reacting Compound 1B with hydrazine hydrate in the presence of an acid.

20. A method of making the antifungal compound of Formula (1) as claimed in claim 2, wherein the antifungal compound is Compound 1E,
said method comprising reacting Compound 1A with hydrazine hydrate in the presence of an acid.

21. A pharmaceutical composition comprising an antifungal compound of Formula 1 as claimed in claim 2, in association with at least one pharmaceutically acceptable excipient.

22. A method for treating a fungal infection in a subject, comprising administering an effective amount of an antifungal compound of Formula (1) as claimed in claim 1, in association with at least one pharmaceutical excipient, and wherein said fungal infection is an infection by at least one fungus selected from the group consisting of *Candida albicans, Candida glabrata, Candida krusei, Candida tropicalis, Candida neoformans, Aspergillus fumigatus, Aspergillus niger* and *Fusarium proliferatum*.

23. A pharmaceutical composition comprising an antifungal compound as claimed in claim 8, in association with at least one pharmaceutically acceptable excipient.

24. A method for treating a fungal infection in a subject, comprising administering an effective amount of an antifungal compound as claimed in claim 8, wherein said fungal infection is an infection by at least one fungus selected from the group consisting of *Candida albicans, Candida glabrata, Candida krusei, Candida tropicalis, Candida neoformans, Aspergillus fumigatus, Aspergillus niger* and *Fusarium proliferatum*.

25. The antifungal compound of Formula (1) as claimed in claim 1, wherein $C^1$ is an alkyl group having from 1 to 14 carbon atoms.

26. The antifungal compound of Formula (1) as claimed in claim 1, wherein $C^1$ is an alkyl group having from 1 to 14 carbon atoms.

* * * * *